US008652786B2

(12) United States Patent
Haber et al.

(10) Patent No.: US 8,652,786 B2
(45) Date of Patent: Feb. 18, 2014

(54) METHOD FOR PREDICTING RESPONSIVENESS TO DRUGS

(75) Inventors: Daniel A. Haber, Chestnut Hill, MA (US); Gromoslaw A. Smolen, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 689 days.

(21) Appl. No.: 11/887,608

(22) PCT Filed: Apr. 5, 2006

(86) PCT No.: PCT/US2006/012678
§ 371 (c)(1),
(2), (4) Date: Nov. 2, 2007

(87) PCT Pub. No.: WO2006/108048
PCT Pub. Date: Oct. 12, 2006

(65) Prior Publication Data
US 2008/0220424 A1 Sep. 11, 2008

Related U.S. Application Data

(60) Provisional application No. 60/681,601, filed on May 17, 2005, provisional application No. 60/668,419, filed on Apr. 5, 2005.

(51) Int. Cl.
*C12Q 1/68* (2006.01)
(52) U.S. Cl.
USPC .................................................. 435/6.14
(58) Field of Classification Search
None
See application file for complete search history.

(56) References Cited

U.S. PATENT DOCUMENTS 7,037,909 B2 * 5/2006 Vojkovsky et al. ........... 514/243

FOREIGN PATENT DOCUMENTS

| WO | WO 03/078662 A1 | 9/2003 |
|----|-----------------|--------|
| WO | WO 2005/070020 A2 | 8/2005 |
| WO | WO 2006/023755 A2 | 3/2006 |

OTHER PUBLICATIONS

Ma et al (Cancer Research, 2003, 63:6272-6281).*
Christensen et al (Cancer Research, 2003, 63:7345-7355) in IDS.*
Di Renzo et al (Clinical Cancer Research, 1995, 1:147-154).*
Lee et al (Oncogene, 2000, 19:4947-5953).*
National Institutes of Health, Genetics Home Reference (p. 1-2, printed Dec. 2009).*
Inoue et al (Cancer Sci, 2004, 95:803-808).*
Nakajima et al (Cancer, 1999, 85:1894-1902).*
R. Abounader et al., Faseb J. 16, 108 (2002). In vivo targeting of SF/HGF and c-met expression via U1snRNA/ ribozymes inhibits glioma growth and angiogenesis and promotes apoptosis.
A. Bertotti, P. M. Comoglio, Trends Biochem. Sci. 28, 527 (2003). Tyrosine kinase signal specificity: lessons from the HGF receptor.
I. Bieche, M. H. Champeme, R. Lidereau, Int. J. Cancer 82, 908 (1999). Infrequent mutations of the MET gene in sporadic breast tumours.
C. Birchmeier, W. Birchmeier, E. Gherardi, G. F. Vande Woude, Nat. Rev. Mol. Cell. Biol. 4, 915 (2003). Met, metastasis, motility and more.
S. G. Brodie et al., Oncogene 20, 7514 (2001). Multiple genetic changes are associated with mammary tumorigenesis in Brca1 conditional knockout mice.
J. G. Christensen et al. Cancer Letters 225, 1-26 (2005) C-met as a target for human cancer and characterization of inhibitors for therapeutic intervention.
J. G. Christensen et al. Cancer Research 63, 7345 (2003) A selective small molecule inhibitor of c-met kinase inhibits c-met-dependent phenotypes in vitro and exhibits cytoreductive antitumor activity in vivo.
M. I. Gallego, B. Bierie, L. Hennighausen, Oncogene 22, 8498 (2003). Targeted expression of HGF/SF in mouse mammary epithelium leads to metastatic adenosquamous carcinomas through the activation of multiple signal transduction pathways.
G. Smolen et al. Proc. Natl. Acad. Sci. U.S.A. 103, 2316 (2006) Amplification of Met may identify a subset of cancers with extreme sensitivity to the selective tyrosine kinase inhibitor PHA-665752.
M. Jeffers et al., Proc. Natl. Acad. Sci. U.S.A. 95, 14417 (1998). The mutationally activated Met receptor mediates motility and metastasis.
J.Y. Kang et al., Cancer Res. 63, 1101 (2003). Tissue Microarray Analysis of Hepatocyte Growth Factor/Met Pathway Components Reveals a Role for Met, Matriptase, and Hepatocyte Growth Factor Activator Inhibitor 1 in the Progression of Node-negative Breast Cancer.
J. H. Lee et al., Oncogene 19, 4947 (2000). A novel germ line juxtamembrane Met mutation in human gastric cancer.
E. Lengyel et al., Int. J. Cancer 113, 678 (2005). C-Met overexpression in node-positive breast cancer identifies patients with poor clinical outcome independent of Her2/neu.
P. C. Ma, G. Maulik, J. Christensen, R. Salgia, Cancer Metastasis Rev. 22, 309 (2003). c-Met: structure, functions and potential for therapeutic inhibition.
P. C. Ma et al. Cancer Research 65, 1479 (2005) Functional Expression and mutations of c-met and its therapeutic inhibition with SU11274 and small interfering RNA in non-small cell lung cancer.

(Continued)

*Primary Examiner* — Laura B Goddard
(74) *Attorney, Agent, or Firm* — David S. Resnick; Shayne Y. Huff; Nixon Peabody LLP

(57) ABSTRACT

The present invention provides a novel method to determine the likelihood of effectiveness of a treatment in an individual affected with or at risk for developing cancer. The method involves detecting the presence or absence of Met amplification in an individual. The presence of Met amplification indicates that a Met targeting treatment is likely to be effective. Preferably, the Met targeting treatment is PHA-665752 or PF-02341066. In addition, the present methods allow for the detection of cancer in an individual, wherein the presence of Met amplification indicates that cancer is present and further that it will be treatable, namely with a Met targeting treatment.

3 Claims, 22 Drawing Sheets

(56) References Cited

OTHER PUBLICATIONS

C. Parr et. al. Intl. J. Oncology 19, 847 (2001) Expression of hepatocyte growth factor/scatter factor, its activator, inhibitors and the c-met receptor in human cancer cells.

S. Rong et al., Mol. Cell. Biol. 12, 5152 (1992). Tumorigenicity of the met proto-oncogene and the gene for hepatocyte growth factor.

S. Rong, S. Segal, M. Anver, J. H. Resau, G. F. Vande Woude, Proc. Natl. Acad. Sci. U.S.A. 91, 4731 (1994). Invasiveness and Metastasis of NIH 3T3 Cells Induced by Met-Hepatocyte Growth Factor/Scatter Factor Autocrine Stimulation.

L. Schmidt et al., Nat. Genet. 16, 68 (1997). Germline and somatic mutations in the tyrosine kinase domain of the MET proto-oncogene in papillary renal carcinomas.

H. Takayama et al., Proc. Natl. Acad. Sci. U.S.A. 94, 701 (1997) Diverse tumorigenesis associated with aberrant development in mice overexpressing hepatocyte growth factor/scatter factor.

X. Xu et al., Nat. Genet. 22, 37 (1999). Conditional mutation of Brca1 in mammary epithelial cells results in blunted ductal morphogenesis and tumour formation.

X. Xu, et al., Nat. Genet. 28, 266 (2001). Genetic interactions between tumor suppressors Brca1 and p53 in apoptosis, cell cycle and tumorigenesis.

Gura (Science, 1997, 278: 1041-1042.).

Bea et al (Cancer Research, Mar. 15, 2001, 61:2409-2412).

Pollack et al (nature Genetics, 1999, 23:41-46).

Di Renzo et al (Clinical Cancer Research, Feb. 1995, 1:147-154).

\* cited by examiner

SEQUENCE LISTING

<160> NUMBER OF SEQ ID NOS: 122

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgttgccaag ctgtattctg tttac                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctctgaatt agagcgatgt tgaca                                          25

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tggataattg tgtctttctc tag                                            23

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccactgcgaa cttaagaaaa ctttg                                          25

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttctctatca cagtcagtcc agatca                                         26

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aacgagagac tcgccagt                                                     18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttccaaccct ctttgattgc a                                                 21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctacttgaa ggccaaatcc tataa                                             25

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
aatccaactg tgaaagat                                                     18

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtttccacac cacctttgat tct                                               23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtcaggagga acacctgtct tca                                               23

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cccactgcag gtgaa                                                        15

```
<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgctacgaag tctgtgacat tcc                                            23

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccattgcag gtcatgcat                                                 19

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cagtgttcag aagttg                                                    16

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtggtctcc tctgacttca aca                                            23

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtggtcgttg agggcaatg                                                 19

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
aaccactcct ccacctttga cgctg                                          25

<210> SEQ ID NO 19
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccacaagccc tgctaatctg ttatt                                              25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctttcttgga gaacaaatta actag                                              25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caccgttatg acaggatttg cacac                                              25

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctgatgact cacagctaaa tgag                                               24

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtcatgtcca accgcacaat gcatc                                              25

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccagtcttgt actcagcaac cttc                                               24

<210> SEQ ID NO 25
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
gtcattctac atgagcatca catt                                          24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgatatcga atgcaatgga tgatc                                         25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cagtgtcctg actgtgtggt gagcg                                         25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcttgctgac atacgcagcc tgaag                                         25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggaaatgcct ctggagtgta ttctc                                         25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtgtaaatg aagattcaat tcctc                                         25

<210> SEQ ID NO 31
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 31
ccttgccatt atcctccagg ctctg                                              25

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cagaaagtag accaggcttc attg                                               24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccacaagccc tgctaatctg ttatt                                              25

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gctgatgact cacagctaaa tgag                                               24

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cttgtttcat taacatgtca tgtag                                              25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttcaagagat gagcttcttg agcaa                                              25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 37
gtcagctcac catttagagt taatg    25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggtacagata ttaattcaaa ttgac    25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gatccagtca gattaaacag cctac    25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caacataaca gcatcaaagc cagag    25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aagttgtttc caaagaacag ttacc    25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctacactgca aggaaattaa ctagc    25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgtgtagtct aacattagga agtta                                              25

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtataagata caatggccaa gtac                                               24

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtatcataga atcgtgtgcc ttggc                                              25

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctaggaatgc aggctgagtt gatg                                               24

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaaggcagtt atgccatttg tagaa                                              25

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
catcgtagcg aactaattca ctg                                                23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccttaagaac acagtcatta cag                                                23

```
<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtgtcaaata cttacttggc agagg                                              25

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gctttcaaaa ttaatactta gtctac                                             26

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cttgttatca ctgctctgtc agttg                                              25

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53 gtactcttt gctgtataga aag                                                 23

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccacaagggg aaagtgtaaa tcaac                                              25

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caagatgcta actgtgtggt ttacc                                              25
```

```
<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gaggtgcatt tgaatgatgc taac                                          24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gaccaaacta atttttgaga caag                                          24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cacatcgatt taagattgta acag                                          24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cttccttcag aagttatgga tttc                                          24

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gaagaaaact ggaattggtg gtgttg                                        26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagaaaccgt attgagtatg taaagc                                        26

<210> SEQ ID NO 62
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcattttagc attacttcat atctg                                          25

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaagactcct acaacccgaa tactg                                          25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
caagtcctat aatagtgcaa ttttg                                          25

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaacacagtc attacagttt aag                                            23

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cttacttggc agaggtaaat acttcc                                         26

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cttagtctac ttaaatgaaa atctg                                          25

<210> SEQ ID NO 68
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 68
ctgctctgtc agttgctttc acc                                             23

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gctgtataga aagaagaaag                                                 20

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cagtggtagc tgatttttcc acaagg                                          26

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ctgtgtggtt taccatttca ttgc                                            24

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gactcagagc aggcctattt tg                                              22

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gaccaaacta atttttgaga caag                                            24

<210> SEQ ID NO 74
<211> LENGTH: 23
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 74
gaaataaagg acttttgcat aag                                                23

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gttatggatt tcaaatactg aagc                                               24

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtccattttt acatatgaag aaaac                                              25

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gagtatgtaa agccaagttt ag                                                 22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cattacttca tatctgttcc aaaaag                                             26

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctgcccagac cccttgtaag tagtc                                              25

<210> SEQ ID NO 80
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 80 gtgcaattttt ggcaagagca aag                                           23

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gatatcgaag ctggaggagt catgc                                          25

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
catagtatgt gtcaacaagc agag                                           24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gttggaacac ccagattgtt tacc                                           24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgaaggcatg tatgtacttt atgg                                           24

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cggctgaagg aaacccaaga tgg                                            23

<210> SEQ ID NO 86
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 86
gacagacgtt tattctgctt catac                                           25

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
catgtgacta tccttgatat tctg                                            24

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gttacccctt tgggttctgt ctctag                                          26

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ctaacaggat gcactgtggg tcttc                                           25

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggaggcatga gtctaagtct cag                                             23

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gatgctactc aattagatgc cgtg                                            24

<210> SEQ ID NO 92
<211> LENGTH: 24
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 92
gatgtccccc acgtagatga atac                                        24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cacacacagg aacacacgca tgtg                                        24

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cctggatgag catgttgaac aattg                                       25

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctcacaattt ggggtttaat atcc                                        24

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gaatcattag tgggagagaa tcacg                                       25

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cttacagatg taattttgga atatg                                       25

<210> SEQ ID NO 98
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 98
cacagcagcg tttaaataaa tgagg                                           25

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gcgagtcctc taacatcata agag                                            24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gtaccatttg acctctgctg cagg                                            24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gtgtaacaac tgatgtgttt tgag                                            24

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gtagaatagg atacactgag cac                                             23

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cagcgtctgc atttgttgta ttcttg                                          26

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 104
gctagagcca acatacagat gagc                                              24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccaccagggt gctaattgga atcc                                              24

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cttttatgaa tgcttattag acaac                                             25

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gttgtctaat aagcattcat aaaag                                             25

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
caggacaaaa agcaaaaagc aag                                               23

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gagtgttccc agcctagcat ttcg                                              24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 110
ctcgttatca ggctctgtca ggag                                              24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gcatggagag aagtgtaatg catc                                              24

<210> SEQ ID NO 112
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ccacaaggga aagtgcaaat gaacac                                            26

<210> SEQ ID NO 113
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tctcttgcta cctaaatttg aaaaag                                            26

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ccttgttaag ggcatttgct actc                                              24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ccacagggca tgagttatta tttg                                              24

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
```

```
cttcgaagag aagagagaaa atgtc                                         25
```

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117

```
caataggcca gaggaaatta tgg                                           23
```

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118

```
gttaccatac aactacggag ag                                            22
```

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119

```
gtgaagtgtg tcaagcaagg atg                                           23
```

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
ccagcatttt agcatcactt cgtac                                         25
```

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

```
ccttgtaagt aagagtttgc tgg                                           23
```

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

```
gttaagtgac cttccaaagg ccag                                          24
```

METHOD FOR PREDICTING RESPONSIVENESS TO DRUGS

CROSS REFERENCE TO RELATED APPLICATIONS

This application is a 371 National Phase Entry Application of International Application PCT/US2006/012678, filed Apr. 5, 2006, which designated the EP, which claims the benefit under 35 U.S.C. §119(e) of U.S. Provisional Patent Application Ser. No. 60/668,419, filed Apr. 5, 2005, and 35 U.S.C. §119(e) of U.S. Provisional Patent Application Ser. No. 60/681,601, filed May 17, 2005 the contents of which are herein incorporated by reference in their entirety.

GOVERNMENT SUPPORT

This invention was made with government support under Grant No. PO1 95281 awarded by the National Institutes for Health (NIH). The Government has certain rights in the invention.

BACKGROUND

Cancers, for example, gastric cancer, prostate cancer, breast cancer, colon cancer, lung cancer, pancreatic cancer, ovarian cancer, cancer of the spleen, testicular cancer, cancer of the thymus, etc., are diseases characterized by abnormal, accelerated growth of epithelial cells. This accelerated growth initially causes a tumor to form. Eventually, metastasis to different organ sites can also occur. Although progress has been made in the diagnosis and treatment of various cancers, these diseases still result in significant mortality.

MET encodes a transmembrane tyrosine kinase receptor for Hepatocyte Growth Factor (HGF, scatter factor), which transduces signals implicated in proliferation, migration and morphogenesis (6-8). Ectopic expression of MET, as well as HGF, confers a tumorigenic and metastatic phenotype in cancer-derived cell lines (9-11), and activating mutations have been reported in both sporadic and inherited forms of renal papillary carcinomas (12). Mutations in MET are rare in breast cancer (13, 14), but tumors with high protein expression appear to have a worse clinical prognosis (15, 16). Furthermore, increased HGF/MET signaling can serve as an initiating event for tumorigenesis, as mice overexpressing either HGF or mutant Met in mammary epithelium develop breast tumors (17-19).

Genetic events that arise and are selected during tumor progression may become essential for tumor survival, a phenomenon generally described as "oncogene addiction" (1). For example, homozygous inactivation of Brca1 alone leads to activation of DNA damage signals and p53-mediated cell cycle arrest; however, simultaneous suppression of p53 allows bypass of this DNA damage checkpoint, and leads to accelerated tumor formation (2-4). The identification of these secondary mutations is important in designing effective treatment for cancers, as targeting one genetic event may not suffice.

It must be remembered that overexpression and amplification are not the same phenomenon. Overexpression can be obtained from a single, unamplified gene, and an amplified gene does not always lead to greater expression levels of mRNA and protein. Thus, it is not possible to predict whether one phenomenon will result in, or is related to, the other. However, in situations where both amplification of a gene and overexpression of the gene product occur in cells or tissues that are in a precancerous or cancerous state, then that gene and its product present both a diagnostic target and a therapeutic opportunity for intervention. Amplification, without overexpression, and overexpression, without amplification, also can be correlated with and indicative of cancers and pre-cancers.

There is a significant need in the art for a satisfactory treatment of cancer, and specifically cancers such as gastric, lung, ovarian, breast, brain, colon and prostate cancers. While tyrosine kinase therapy has proven to be beneficial in many cancer types, its utility is currently limited by our understanding of the individuals in which the therapy is most likely to be effective. Thus, there is a need to identify patients who will most benefit from particular therapies, so as, for example, to limit clinical trial participation to only this subset of individuals and to provide the most appropriate therapy to each individual person in need.

SUMMARY

The inventors of the present invention have surprisingly discovered that the presence of Met amplification predicts responsiveness of an individual to Met targeted treatment. Thus, the present invention provides a novel method to determine the likelihood of effectiveness of a Met targeting treatment in an individual affected with or at risk for developing cancer. The method comprises detecting the presence or absence of Met amplification of said individual. The presence of Met amplification indicates that the Met targeting treatment is likely to be effective. In addition, the present methods allow for the detection of cancer in an individual, wherein the presence of Met amplification indicates that cancer is present and further that it will be treatable namely with a Met targeting treatment.

In a preferred embodiment, the Met targeting treatment is a tyrosine kinase inhibitor. In a preferred embodiment, the tyrosine kinase inhibitor is a Met tyrosine kinase inhibitor. Preferably, the Met tyrosine kinase inhibitor PHA-665752, (3Z)-5-[(2,6-dichlorobenzyl)sulfonyl]-3-[(3,5-dimethyl-4-{[(2R)-2-(pyrrolidin-1-ylmethyl)pyrrolidin-1-yl]carbonyl}-1H-pyrrol-2-yl)methylene]-1,3-dihydro-2H-indol-2-one (Pfizer, Inc., La Jolla, Calif.). Alternatively, the Met targeting treatment is PF-02341066 (Pfizer, Inc.) or one or more of the c-Met inhibitors described in U.S. Patent Application 20050107391. Also encompassed in the present invention is XL880, an orally available Spectrum Selective Kinase Inhibitor™ (SSKI) from Exelixis. Other Met targeting treatments are known to those of skill in the art and are encompassed herein.

Also encompassed in the present invention are methods of treating an individual affected with or at risk for developing cancer. In this embodiment, an individual is screened for the presence or absence of Met amplification. Individuals identified with Met amplification are therein administered a Met targeting treatment. In one embodiment, the Met targeting treatment is a tyrosine kinase inhibitor. In a preferred embodiment, the Met targeting treatment is a Met inhibitor. The Met inhibitor may be selected from the group consisting of a small molecule inhibitor, a competitive inhibitor, a nucleic acid, an antibody, an antibody fragment, or an aptamer.

Alternatively, the status of Met amplification in an individual is known and a treatment plan is initiated based on this known status. In this embodiment, the presence of Met amplification indicates that a Met targeting treatment will be effective in the treatment or prevention of a cancer. Thus, a Met targeting treatment can be administered to such an individual. Thus, once a patient has been identified as having Met amplification (e.g. the test was done by another physician, at another clinic, or in another country), a Met targeting treatment can be administered.

In one embodiment, the Met amplification assay is performed outside the country of treatment, e.g., the U.S., and the results are provided to the physician, patient or clinic. The results can be sent electronically or can be resident on a web site and screened by the physician, clinic or patient.

The detection of the presence or absence of a Met amplification is accomplished by determining the copy number of the Met gene. In one embodiment the copy number is compared to a positive and negative control sample. The copy number of Met gene may be determined by PCR, qPCR, RT-PCR, Southern Blot, comparative genomic hybridization, microarray based comparative genomic hybridization, fluorescence in situ hybridization (FISH), ligase chain reaction (LCR), transcription amplification, or self-sustained sequence replication.

The cancer may be any cancer known to those of skill in the art, including, but not limited to, gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer. In a preferred embodiment, the cancer is non-small cell lung cancer.

Also encompassed in the methods of the present invention is a kit for detecting the presence or absence of Met amplification.

DESCRIPTION OF THE FIGURES

FIG. 1: Recurrent amplification in primary mammary tumors of Brca1$^{\Delta 11/co}$ Trp53$^{+/-}$ MMTV-Cre mice spanning the Met oncogene locus.

FIG. 2: MET genomic amplification in human gastric cancer.

FIG. 3: Constitutive activation of MET and activation of downstream signaling pathways in Amp$^+$ cells.

FIG. 4: Gastric cancer cell lines with MET amplification display selective killing following MET inhibition.

FIG. 8: MET genomic amplification in human gastric cancer cell lines.

FIG. 9: Constitutive activation of MET in Amp+ cells.

FIG. 10: Selective killing of gastric cancer cell lines with MET amplification after MET inhibition.

FIG. 11: Suppression of MET-dependent signals by PHA-665752 in Amp+ cells and induction of apoptosis.

DETAILED DESCRIPTION

Figure 1A:
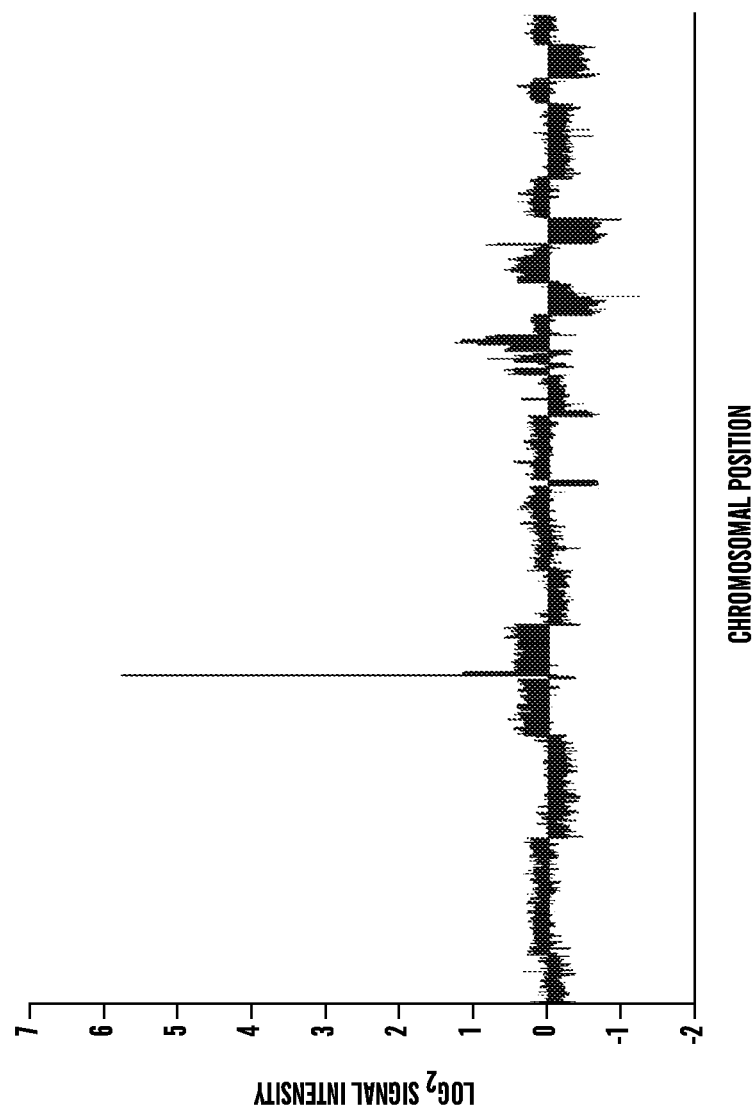
(FIG. 1A) Representative whole genome profile of an individual tumor showing the ratio of tumor to normal DNA from the same mouse. X-axis represents oligonucleotide probes ordered by genomic map position, with the whole-genome filtered median (three nearest neighbors) data set plotted on the Y axis.

The present invention provides a novel method to determine the likelihood of effectiveness of an Met targeting treatment in an individual affected with or at risk for developing cancer. The method comprises detecting the presence or absence of Met amplification of said individual. The presence of Met amplification indicates that the Met targeting treatment is likely to be effective. The individual with Met amplification can then be treated with a Met targeting treatment.

In one embodiment of the present invention, the Met targeting treatment is a tyrosine kinase inhibitor. In a preferred embodiment, the tyrosine kinase inhibitor is a Met tyrosine kinase inhibitor. Preferably, the Met tyrosine kinase inhibitor PHA-665752, (3Z)-5-[(2,6-dichlorobenzyl)sulfonyl]-3-[(3,5-dimethyl-4-{[(2R)-2-(pyrrolidin-1-ylmethyl)pyrrolidin-1-yl]carbonyl}-1H-pyrrol-2-yl)methylene]-1,3-dihydro-2H-indol-2-one (Pfizer, Inc., La Jolla, Calif.) or SU11274. Alternatively, the Met targeting treatment is PF-02341066 (Pfizer, Inc.) or one or more of the c-Met inhibitors described in U.S. Patent Application 20050107391, incorporated by reference in its entirety. In an alternative embodiment of the present invention, the Met targeting treatment is an indirect modulator of Met, such as, for example, SU5416, which targets vascular endothelial growth factor (VEGF) and has been shown to display activity against Met.

The methods of the present method allow for the screening of individuals with or at risk for developing cancer, including, but not limited to, solid tumor, solid tumor metastasis and the like. Individuals who have already been diagnosed with cancer are encompassed in the methods of the present invention. Cancers include, but are not limited to, breast, lung, colorectal, prostate, pancreatic, glioma, liver cancer, gastric cancer, head and neck cancers, melanoma, renal cancer, leukemias, myeloma, and sarcomas. Met has been directly implicated in cancers without a successful treatment regimen such as pancreatic cancer, glioma, and hepatocellular carcinoma. medulloblastoma, and mesothelioma. The strong correlation of Met with the biology of metastasis and invasion and disease pathogenesis comprises a novel mechanism for determination of likelihood of drug responsiveness to metastatic cancers.

Detection Methods

According to the methods of the present invention, detecting the presence or absence of Met amplification in a patient with or at risk for developing cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods.

Gene amplification is a quantitative modification, whereby the actual number of complete coding sequence, i.e. a gene, increases, leading to an increased number of available templates for transcription, an increased number of translatable transcripts, and, ultimately, to an increased abundance of the protein encoded by the amplified gene.

Gene amplification is most commonly encountered in the development of resistance to cytotoxic drugs (antibiotics for bacteria and chemotherapeutic agents for eukaryotic cells) and neoplastic transformation. Transformation of a eulcaryotic cell as a spontaneous event or due to a viral or chemical/environmental insult is typically associated with changes in the genetic material of that cell.

The presence of a target gene that has undergone amplification in tumors is evaluated by determining the copy number of the target genes, i.e., the number of DNA sequences in a cell encoding the target protein. Generally, a normal diploid cell has two copies of a given autosomal gene. The copy number can be increased, however, by gene amplification or duplication, for example, in cancer cells, or reduced by deletion. Methods of evaluating the copy number of a particular gene are well known in the art, and include, hybridization and amplification based assays.

Detection and measurement of amplification of the MET gene in a test sample taken from a patient indicates that the patient may have developed a tumor. According to the present invention, the presence of Met amplification predicts the likelihood of effectiveness of Met targeting therapy. Particularly, the presence of amplified MET DNA leads to a diagnosis of cancer or precancerous condition, for example, a gastric cancer, a breast cancer, a colon cancer, a lung cancer, a brain cancer, or an ovarian cancer where Met targeting therapy is likely to be effective.

The present invention therefore provides, in one aspect, methods for detecting Met amplification. In one embodiment, Met amplification is detected by measuring the levels of MET mRNA expression in samples taken from the tissue of suspicion, and determining whether MET is overexpressed in the tissue. The various techniques, including hybridization based and amplification based methods, for measuring and evaluating mRNA levels are provided herein and are known to those of skill in the art.

The present invention also provides, in other aspects, methods for detecting Met amplification in a mammalian tissue by measuring the numbers of MET DNA copy in samples taken from the tissue of suspicion, and determining whether the MET gene is amplified in the tissue. The various techniques, including hybridization based and amplification based methods, for measuring and evaluating DNA copy numbers are provided herein and known to those of skill in the art. The present invention thus provides methods for detecting amplified genes at the DNA level and increased expression at the RNA level, or increased protein expression wherein the results are indicative of tumor progression.

Detecting Gene Amplification

The present invention encompasses methods of gene amplification known to those of skill in the art, see, for example, Boxer, J. Clin. Pathol. 53: 19-21 (2000). Such techniques include in situ hybridization (Stoler, Clin. Lab. Med. 12:215-36 (1990), using radioisotope or fluorophore-labeled probes; polymerase chain reaction (PCR); quantitative Southern blotting, dot blotting and other techniques for quantitating individual genes. Preferably, probes or primers selected for gene amplification evaluation are highly specific, to avoid detecting closely related homologous genes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In one embodiment, the biological sample contains nucleic acids from the test subject. The nucleic acids may be mRNA or genomic DNA molecules from the test subject.

In another embodiment, the methods further involve obtaining a control biological sample and detecting Met amplification in this control sample, such that the presence or absence of Met amplification in the control sample is determined. A negative control sample is useful if there is an absence of Met amplification, whereas a positive control sample is useful if there is a presence of Met amplification. For the negative control, the sample may be from the same individual as the test sample (i.e. different location such as tumor versus non-tumor) or may be from a different individual known to have an absence of Met amplification.

In a preferred embodiment of the present invention, gene amplification is detected by polymerase chain reaction (PCR)-based assays. These assays utilize a very small amount of tumor DNA as starting material, are exquisitely sensitive and provide DNA that is amenable to further analysis, such as sequencing, and are suitable for high-volume throughput analysis.

Amplification-Based Assays

In one embodiment of the present invention, amplification-based assays can be used to measure copy number of the MET gene. In such amplification-based assays, the corresponding MET nucleic acid sequence acts as a template in an amplification reaction (for example, Polymerase Chain Reaction or PCR). In a quantitative amplification, the amount of amplification product will be proportional to the amount of template in the original sample. Comparison to appropriate controls provides a measure of the copy-number of the MET gene, corresponding to the specific probe used. The presence of a higher level of amplification product, as compared to a control, is indicative of amplified Met.

Quantitative PCR

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990) PCR Protocols, A Guide to Methods and Applications, Academic Press, Inc. N.Y. The known nucleic acid sequence for the Met (Accession No.: NM_000245) is sufficient to enable one of skill to routinely select primers to amplify any portion of the gene.

Real Time PCR

Real time PCR is another amplification technique that can be used to determine gene copy levels or levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For gene copy levels, total genomic DNA is isolated from a sample. For mRNA levels, mRNA is extracted from tumor and normal tissue and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from $10$-$10^6$ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

A TaqMan-based assay also can be used to quantify MET polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, Ampli-Taq, results in the cleavage of the TaqMan probe. This cleavage separates the 5' fluorescent dye and the 3' quenching agent, thereby resulting in an increase in fluorescence as a function of amplification.

Other Amplification Methods

Other suitable amplification methods include, but are not limited to ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc.

Hybridization-Based Assays

Hybridization assays can be used to detect MET copy number. Hybridization-based assays include, but are not limited to, traditional "direct probe" methods such as Southern blots or in situ hybridization (e.g., FISH), and "comparative probe" methods such as comparative genomic hybridization (CGH). The methods can be used in a wide variety of formats including, but not limited to substrate—(e.g. membrane or glass) bound methods or array-based approaches as described below.

Southern Blot

One method for evaluating the copy number of Met encoding nucleic acid in a sample involves a Southern transfer. Methods for doing Southern Blots are known to those of skill in the art (see Current Protocols in Molecular Biology, Chapter 19, Ausubel, et al., Eds., Greene Publishing and Wiley-Interscience, New York, 1995, or Sambrook et al., Molecular Cloning: A Laboratory Manual, 2d Ed. vol. 1-3, Cold Spring Harbor Press, NY, 1989). In such an assay, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. An intensity level that is higher than the control is indicative of amplified Met.

Fluorescence In Situ Hybridization (FISH)

In another embodiment, FISH is used to determine the copy number of the MET gene in a sample. Fluorescence in situ hybridization (FISH) is known to those of skill in the art (see Angerer, 1987 Meth. Enzymol., 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments.

In a typical in situ hybridization assay, cells or tissue sections are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

In some applications it is necessary to block the hybridization capacity of repetitive sequences. Thus, in some embodiments, tRNA, human genomic DNA, or Cot-1 DNA is used to block non-specific hybridization. Thus, in one embodiment of the present invention, the presence or absence of Met amplification is determined by FISH.

Comparative Genomic Hybridization (CGH)

In comparative genomic hybridization methods, a "test" collection of nucleic acids (e.g. from a possible tumor) is labeled with a first label, while a second collection (e.g. from a normal cell or tissue) is labeled with a second label. The ratio of hybridization of the nucleic acids is determined by the ratio of the first and second labels binding to each fiber in an array. Differences in the ratio of the signals from the two labels, for example, due to gene amplification in the test collection, is detected and the ratio provides a measure of the gene copy number, corresponding to the specific probe used. A cytogenetic representation of DNA copy-number variation can be generated by CGH, which provides fluorescence ratios along the length of chromosomes from differentially labeled test and reference genomic DNAs. In another embodiment of the present invention, comparative genomic hybridization may be used to detect the presence or absence of Met amplification.

Microarray Based Comparative Genomic Hybridization

In an alternative embodiment of the present invention, DNA copy numbers are analyzed via microarray-based platforms. Microarray technology offers high resolution. For example, the traditional CGH generally has a 20 Mb limited mapping resolution; whereas in microarray-based CGH, the fluorescence ratios of the differentially labeled test and reference genomic DNAs provide a locus-by-locus measure of DNA copy-number variation, thereby achieving increased mapping resolution. Details of various microarray methods can be found in the literature. See, for example, U.S. Pat. No. 6,232,068; Pollack et al., Nat. Genet., 23(1):41-6, (1999), Pastinen (1997) Genome Res. 7: 606-614; Jackson (1996) Nature Biotechnology 14:1685; Chee (1995) Science 274: 610; WO 96/17958, Pinkel et al. (1998) Nature Genetics 20: 207-211 and others.

The DNA used to prepare the arrays of the invention is not critical. For example, the arrays can include genomic DNA, e.g. overlapping clones that provide a high resolution scan of a portion of the genome containing the desired gene, or of the gene itself. Genomic nucleic acids can be obtained from, e.g., HACs, MACs, YACs, BACs, PACs, P1s, cosmids, plasmids, inter-Alu PCR products of genomic clones, restriction digests of genomic clones, cDNA clones, amplification (e.g., PCR) products, and the like. Arrays can also be produced using oligonucleotide synthesis technology. Thus, for example, U.S. Pat. No. 5,143,854 and PCT Patent Publication Nos. WO 90/15070 and WO 92/10092 teach the use of light-directed combinatorial synthesis of high density oligonucleotide arrays.

Hybridization protocols suitable for use with the methods of the invention are described, e.g., in Albertson (1984) EMBO J. 3: 1227-1234; Pinkel (1988) Proc. Natl. Acad. Sci. USA 85: 9138-9142; EPO Pub. No. 430,402; Methods in Molecular Biology, Vol. 33: In Situ Hybridization Protocols, Choo, ed., Humana Press, Totowa, N.J. (1994), Pinkel et al. (1998) Nature Genetics 20: 207-211, or of Kallioniemi (1992) Proc. Natl. Acad Sci USA 89:5321-5325 (1992), etc.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Kits

In another embodiment of the present invention, kits useful for the detection of Met amplification are disclosed. Such kits may include any or all of the following: assay reagents, buffers, specific nucleic acids or antibodies (e.g. full-size monoclonal or polyclonal antibodies, single chain antibodies (e.g., scFv), or other gene product binding molecules), and other hybridization probes and/or primers, and/or substrates for polypeptide gene products.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Method of Treating a Patient

In one embodiment, the invention provides a method for selecting a treatment for a patient affected by or at risk for developing cancer by determining the presence or absence of amplified Met.

In certain embodiments, the presence of amplified MET is indicative that a Met targeting treatment will be effective or otherwise beneficial (or more likely to be beneficial) in the individual. Stating that the treatment will be effective means that the probability of beneficial therapeutic effect is greater than in a person not having the appropriate presence MET amplification.

In one embodiment, the treatment involves the administration of a tyrosine kinase inhibitor. In particular, the tyrosine kinase inhibitor is a MET tyrosine kinase inhibitor. The treatment may involve a combination of treatments, including, but not limited to a tyrosine kinase inhibitor in combination with other tyrosine kinase inhibitors, chemotherapy, radiation, etc.

Thus, in connection with the administration of a tyrosine kinase inhibitor, a drug which is "effective against" a cancer indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

Met Targeting Treatments

In one embodiment of the present invention, the Met targeting treatment is a tyrosine kinase inhibitor. Alternatively and preferably, the Met targeting treatment is specific for the inhibition of Met. For example, a small molecule inhibitor, a competitive inhibitor, an antibody, or a nucleic acid which inhibits Met. In one embodiment of the present invention, the Met targeting treatment is PHA-665752 [(3Z)-5-[(2,6-dichlorobenzyl)sulfonyl]-3-[(3,5-dimethyl-4-{[(2R)-2-(pyrrolidin-1-ylmethyl)pyrrolidin-1-yl]carbonyl}-1H-pyrrol-2-yl)methylene]-1,3-dihydro-2H-indol-2-one (Pfizer, Inc., La Jolla, Calif.); Christensen et al., Cancer Research 63: 7345-7355, (2003)], SU11274 [Sattler et al., Cancer Research 63: 5462-5469 (2003)], or SU5416 [Fong et al., Cancer Research 59:99-106 (1999); Wang et al., J Hepatol 41: 267-273 (2004)]. In a preferred embodiment, the Met targeting treatment is PF-02341066 (Pfizer, Inc.).

Also encompassed in the present invention are c-Met inhibitors described in U.S. patent application 20050107391, incorporated herein by reference in its entirety.

The reversible phosphorylation of tyrosine residues on proteins is an important mechanism of signal transduction. A large variety of natural and synthetic compounds are known to be tyrosine kinase inhibitors. Almost all of these inhibitors block protein kinases by blocking the ATP pocket of the enzymes. Therefore, many have a broad spectrum of activity not only against tyrosine kinases but also against serine/threonine kinases and/or other ATP utilizing proteins. In one embodiment of the present invention, the Met targeting treatment is one such tyrosine kinase inhibitor and may be selected from the following: a member of the geldanamycin family of anisamycin antibiotics, which have been implicated in the down-regulation of the MET at nanomolar concentrations. This class of compounds are currently in clinical trials (NCI) as potential anti-invasive, anti-metastatic agents and are encompassed in the methods of the present invention.

In addition, other examples of Met targeting treatments encompassed in the methods of the present invention are tyrosine kinase inhibitors such as, but not limited to, indrocarbazoles, such as K252a, which is known to inhibit Met mediated signals at nanomolar concentrations, The compound inhibits Met autophosphorylation and prevents activation of its downstream effectors MAPKinase and Akt. It prevents HGF-mediated scattering in MLP-29 cells, reduces Met-driven proliferation in GTL-16 gastric carcinoma cells, and reverses Met mediated transformation of NIH3T3 fibroblasts. K252a and related compounds are promising leads of drugs that may be used against Trk and Met driven cancers [Morotti et al., Oncogene 21:4885-4893, (2002)]. Conceivably, K252a may serve as a lead in the development of Met specific inhibitors.

Also encompassed in the methods of the present invention are inhibitors with selectivity for protein tyrosine kinases. Several classes of compounds are known protein tyrosine kinase inhibitors and my be used in the methods of the present invention. For example, genistein, lavendustin A, tyrphostin 47, herbimycin, staurosporin and radicicol. Herbimycin A is a benzoquinoid ansamycin antibiotic that inhibits a broad spectrum of protein tyrosine kinases by covalently interacting with their kinase domains. Staurosporin is an indole carbazole antibiotic which inhibits a broad spectrum of kinases including scr family members, and serine/threonine kinases. More recently a large number of protein tyrosine kinase inhibitors have been described, all of which are encompassed in the methods of the present invention; 1) bis monocyclic, bicyclic or heterocyclic aryl compounds (WO 92/20642); 2) vinylene-azaindole derivatives (WO 94/14808); 3) 1-cyclopropyl-4-pyridyl-quinolones (U.S. Pat. No. 5,330,992); 4) styryl compounds (U.S. Pat. No. 5,217,999); 2) styryl-substituted pridyl compounds (U.S. Pat. No. 5,302,606); 5) quinazoline derivatives (EP Application No. 0 566 266A1 and U.S. Pat. No. 6,103,728); 6) selenoindoles and selenides (WO 94/03427); 7) tricyclic polyhydroxylic compounds (PCT WO 92/21660); 8) benzylphosphonic acid compounds (PCT WO 91/15495); 9) tyrphostin like compounds (U.S. Pat. No. 6,225,346B1); 10) thienyl compounds (U.S. Pat. No. 5,886, 195); and 11) bezodiazepine based compounds (U.S. Pat. No. 6,100,254).

Other tyrosine kinase inhibitors encompassed in the present invention include, but are not limited to the pyrazole pyrimidine PP1, STI-571 (GLEEVEC™), ZD1839, OSI-774, SU101, Aryl and heteroaryl quinazoline compounds, SU 5416, Bis mono- and bicyclic aryl and hetero aryl compounds show selectivity for EGFR and PDGFR (U.S. Pat. No. 5,409, 930), Piceatannol (3,4,3,5V-tetrahydroxy-rans-stilbene), and benzodiazepines. Other useful inhibitors include RNA ligands (Jellinek, et al., Biochemistry 33:10450-56; Takano, et al., 1993, Mol. Bio. Cell 4:358A; Kinsella, et al. 1992, Exp. Cell Res. 199:56-62; Wright, et al., 1992, J. Cellular Phys. 152:448-57) and various other tyrosine kinase inhibitors as disclosed in WO 94/03427; WO 92/21660; WO 91/15495; WO 94/14808; U.S. Pat. No. 5,330,992; and Mariani, et al., 1994, Proc. Am. Assoc. Cancer Res. 35:2268.

Also encompassed in the methods of the present invention are methods for the identification of Met tyrosine kinase inhibitors. Methods include, but are not limited to, the use of mutant ligands (U.S. Pat. No. 4,966,849) and soluble receptors and antibodies (Application No. WO 94/10202; Kendall & Thomas, 1994, Proc. Natl. Acad. Sci. 90:10705-09; Kim et al., 1993, Nature 362:841-844).

In another embodiment of the present invention, the Met targeting treatment is a small molecule inhibitor. For example, bis monocyclic, bicyclic or heterocyclic aryl compounds (WO 92/20642) and vinylene-azaindole derivatives (WO 94/14808) have been described generally as tyrosine kinase inhibitors. Styryl compounds (U.S. Pat. No. 5,217, 999), styryl-substituted pyridyl compounds (U.S. Pat. No. 5,302,606), certain quinazoline derivatives (EP Application No. 0 566 266 A1; Expert Opin. Ther. Pat. (1998), 8(4): 475-478), selenoindoles and selenides (WO 94/03427), tricyclic polyhydroxylic compounds (WO 92/21660) and benzylphosphonic acid compounds (WO 91/15495) have been described as compounds for use as tyrosine kinase inhibitors for use in the treatment of cancer. Anilinocinnolines (WO 97/34876) and quinazoline derivative compounds (WO 97/22596; WO 97/42187) have been described as inhibitors of angiogenesis and vascular permeability.

Other Met targeting treatments useful in the methods of the present invention include nucleic acid ligands to HGF and MET, such as those described in PCT International Publication No. WO 01/09159. Also encompassed in the present invention are MET antagonists described in U.S. Pat. Nos. 5,686,292 and 6,099,841, U.S. Pat. No. 6,174,889, PCT International Publication Nos. WO 00/43373, WO 98/07695 and WO 99/15550.

Particularly useful in the methods of the present invention are compounds which inhibit Met specifically. Inhibitors which modulate MET have been reported and include, but are not limited to the following: indolinone hydrazides (WO05/005378), tetracyclic compounds (WO05/004808; U.S. published patent application No. 2005/0014755), arylmethyl triazolo and imidazopyrazines (WO05/004607), triazolotriazine compounds (WO05/010005), pyrrole compositions (WO05/016920), aminoheteroaryl compounds (WO04/076412; U.S.

published patent application No. 2005/0009840), 4,6-diaminosubstituted-2-[oxy or aminoxy]-[1,3,5]triazines (WO04/031184), triarylimidazoles (U.S. published patent application No. 2005/0085473), 2-(2,6-dichlorophenyl)-diarylimidazoles (U.S. published patent application No. 2004/0214874; U.S. published patent application No. 2003/0199691), nucleic acids (U.S. published patent application No. 2003/0049644; U.S. Pat. No. 6,344,321; U.S. Pat. No. 5,646,036; WO01/09159), antibodies (U.S. Pat. No. 5,686,292; U.S. Pat. No. 5,646,036; U.S. published patent application No. 2004/0166544; U.S. published patent application No. 2005/0054019; WO05/016382; WO04/072117), peptide and polypeptides (U.S. Pat. No. 6,214,344; U.S. published patent application No. 2003/0118587; U.S. published patent application No. 2002/0136721 WO04/078778; WO05/030140) and others described in U.S. published patent application No. 2004/0210041; U.S. published patent application No. 2003/0118585; U.S. published patent application No. 2003/0045559; U.S. published patent application No. 2004/0185050.

Other MET inhibitors which can be used in the methods of the invention include but are not limited to the following: substituted 2,3-dihydro-1 h-isoindol-1-one derivatives (U.S. published patent application No. 2005/0054670); Geometrically restricted 3-cyclopentylidene-1,3-dihydroindol-2-ones (U.S. published patent application No. 2005/0038066), Substituted quinolinone derivatives (U.S. published patent application No. 2005/0049253), 5-sulfonamido-substituted indolinone compounds (U.S. published patent application No. 2004/0204407), Cyclic substituted fused pyrrolocarbazoles and isoindolones (U.S. published patent application No. 2004/0186157), Heterocyclic compounds (U.S. published patent application No. 2004/0209892), Indazolinone compositions (U.S. published patent application No. 2004/0167121), Heterocyclic substituted pyrazolones (U.S. published patent application No. 2003/0162775), Benzothiazole derivatives (U.S. published patent application No. 2003/0153568), Pyrazolopyrimidines (U.S. published patent application No. 2002/0156081) and others (U.S. published patent application No. 2004/0116388; U.S. published patent application No. 2004/0019067; U.S. published patent application No. 2003/0004174; U.S. published patent application No. 2003/0199534; U.S. published patent application No. 2002/0052386; U.S. published patent application No. 2003/0069430; U.S. published patent application No. 2004/0198750; U.S. published patent application No. 2004/0127453)

In another aspect, the invention concerns an article of manufacture or package, comprising a container, a composition within the container comprising a MET antagonist, e.g., an anti-MET antibody (or other anti-tumor-specific antigen antibody), optionally a label on or associated with the container that indicates that the composition can be used for treating a condition characterized by overexpression of MET, and a package insert containing instructions to administer the antagonist to patients who have been found to have an amplified MET gene. A therapeutic product may include sterile saline or another pharmaceutically acceptable emulsion and suspension base.

Once identified, such compounds are administered to patients in need of Met targeted treatment, for example, patients affected with or at risk for developing cancer or cancer metastasis.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The compounds of the invention can be administered parenterally by injection or by gradual infusion over time and can be delivered by peristaltic means.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

For topical administration, the pharmaceutical composition (inhibitor of kinase activity) is formulated into ointments, salves, gels, or creams, as is generally known in the art.

The therapeutic compositions of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

The tyrosine kinase inhibitors useful for practicing the methods of the present invention are described herein. Any formulation or drug delivery system containing the active ingredients, which is suitable for the intended use, as are generally known to those of skill in the art, can be used. Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

DEFINITIONS

The term "drug" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "genotype" in the context of this invention refers to the particular allelic form of a gene, which can be defined by the particular nucleotide(s) present in a nucleic acid sequence at a particular site(s).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

The term "antibody" is meant to be an immunoglobulin protein that is capable of binding an antigen. Antibody as used herein is meant to include antibody fragments, e.g. F(ab')2, Fab', Fab, capable of binding the antigen or antigenic fragment of interest. Preferably, the binding of the antibody to the antigen inhibits the activity of a variant form of EGFR.

The term "humanized antibody" is used herein to describe complete antibody molecules, i.e. composed of two complete light chains and two complete heavy chains, as well as antibodies consisting only of antibody fragments, e.g. Fab, Fab', F (ab')$_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human patient.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species.

Preferably, the variable region is derived from a non-human mammalian species and the constant region is derived from a human species. Specifically, the chimeric antibody is preferably produced from a 9 nucleotide sequence from a non-human mammal encoding a variable region and a nucleotide sequence from a human encoding a constant region of an antibody.

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

The phrases "gene amplification" and "gene duplication" are used interchangeably and refer to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The "copy number of a gene" refers to the number of DNA sequences in a cell encoding a particular gene product. Generally, for a given gene, an animal has two copies of each gene. The copy number can be increased, however, by gene amplification or duplication, or reduced by deletion.

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

To "compare" levels of gene expression means to detect gene expression levels in two samples and to determine whether the levels are equal or if one or the other is greater. A comparison can be done between quantified levels, allowing statistical comparison between the two values, or in the absence of quantification, for example using qualitative methods of detection such as visual assessment by a human.

The term "antagonist" is used in the broadest sense, and includes any molecule that partially or fully blocks, inhibits, or neutralizes a biological activity of MET or the transcription or translation thereof. Suitable antagonist molecules specifically include antagonist antibodies or antibody fragments, fragments, peptides, small organic molecules, anti-sense nucleic acids, etc.

"Reducing the level of gene activity" refers to inhibiting the gene product activity in the cell, or lowering the copy number of the gene, or decreasing the level of the gene's transcribed mRNA or translated protein in the cell. Preferably, the level of the particular gene activity is lowered to the level typical of a normal, cancer-free cell, but the level may be reduced to any level that is sufficient to decrease the proliferation of the cell, including to levels below those typical of normal cells.

An "inhibitor of gene activity" is a molecule that acts to reduce or prevent the production and/or accumulation of gene product activity in a cell. The molecule can prevent the accumulation at any step of the pathway from the gene to enzyme activity, e.g. preventing transcription, reducing mRNA levels, preventing translation, or inhibiting the enzyme itself. Such inhibitors can include antisense molecules or ribozymes, repressors of gene transcription, or competitive or non-competitive molecular inhibitors of the gene product.

The phrase "repressor of transcription" refers to a molecule that can prevent the production of mRNA from a particular gene. Preferably, the molecule binds directly or indirectly to a regulatory element of the gene, thereby preventing the transcription of the gene.

The terms "HGF receptor" and "c-Met" and "Met" when used herein refer to a cellular receptor for HGF, which typically includes extracellular domain, a transmembrane domain and an intracellular domain, as well as variants and fragments thereof which retain the ability to bind HGF. The terms "HGF receptor" and "c-Met" and "Met" include the polypeptide molecule that comprises the full-length, native amino acid sequence encoded by the gene variously known as $p190^{MET}$. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence identity, and more preferably at least about 75% sequence identity with any domain of the human c-Met amino acid sequence published in Rodrigues et al., Mol. Cell. Biol. 11:2962-2970 (1991); Park et al., Proc. Natl. Acad. Sci., 14:6379-6383 (1987); or Ponzetto et al., Oncogene 6:553-559 (1991). The nucleic acid sequence of the polynucleotide encoding the full-length protein of MET was published by Park et al. (Proc. Natl. Acad. Sci. USA 84: 6379-83 (1987)) and submitted to GenBank under the accession number NM 000245.

EXAMPLES

Example 1

Figure 1B:
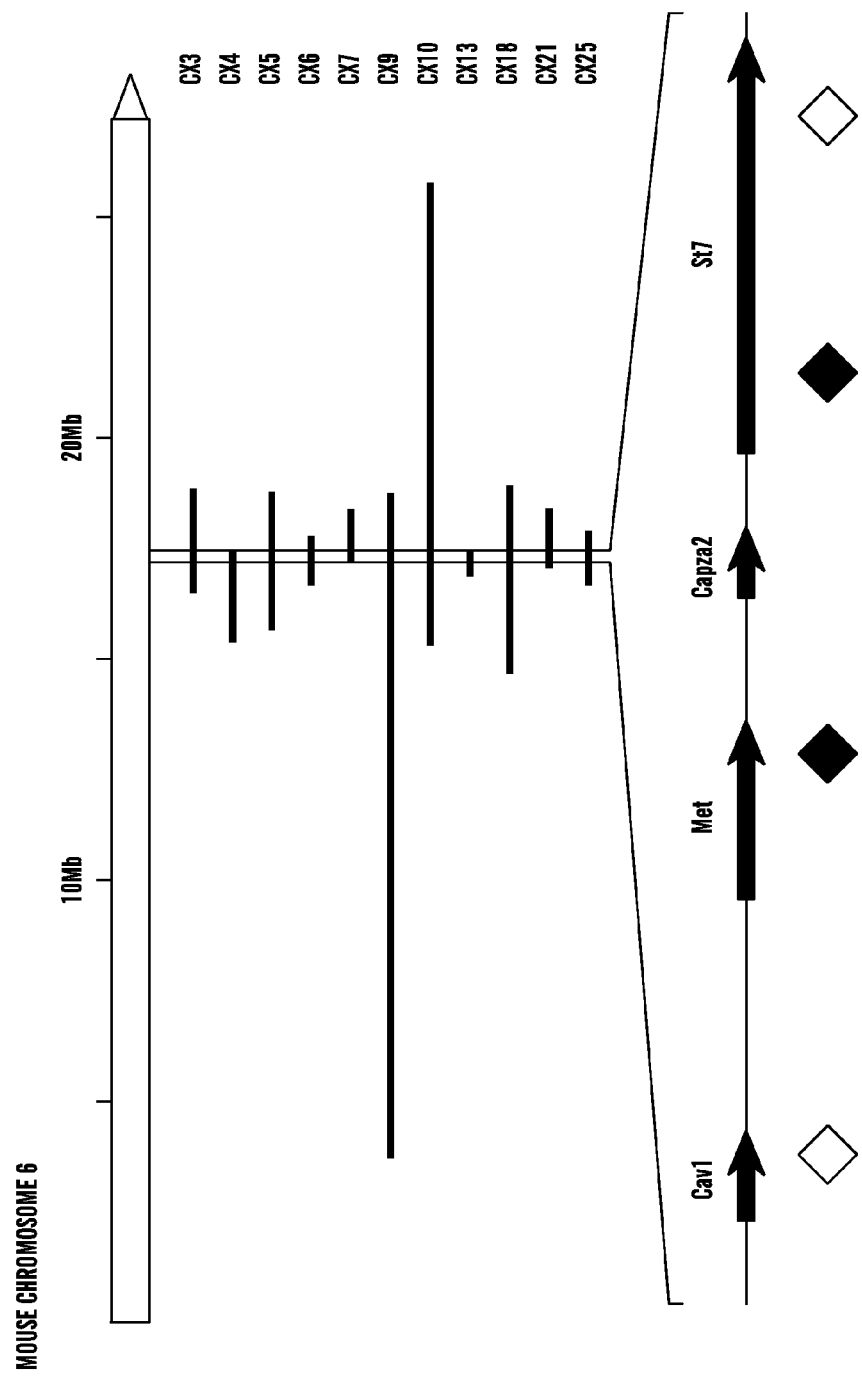
(FIG. 1B) Schematic representation of the minimally amplified region derived from the analysis of individual tumor data sets. Only two complete genes are found in the minimal amplicon. Horizontal bars represent the amplified region in individual tumor samples (CX3-25); vertical lines demarcate the region shared by all amplicons, which is expanded at the bottom of the panel. The positions of oligonucleotide probe targets present on the microarray are shown for those amplified in all 11/15 tumors (black diamonds) and those found not to be amplified in at least one of the 11 tumors (open diamonds).

Mouse mammary tumors derived from a heterozygous Trp53 deletion with a tissue-specific deletion of Brca1 (Brca1$^{\Delta 11/co}$ Trp53$^{+/-}$ MMTV-Cre)(2) were subjected to a whole-genome survey using long oligonucleotide microarrays (Agilent). The use of coding sequence markers for genomic copy number analysis has proven highly effective in identifying gene-centered amplifications and deletions (5). Remarkably, a single recurrent abnormality was evident in 11 of 15 (73%) tumors, namely high level amplification of a locus on chromosome 6 (FIG. 1A). The minimal amplicon contained only two full-length genes—Capza2, encoding the F-actin capping protein alpha-2 subunit involved in cytoskeleton remodeling, and the oncogene Met (FIG. 1B).

Figure 1C:
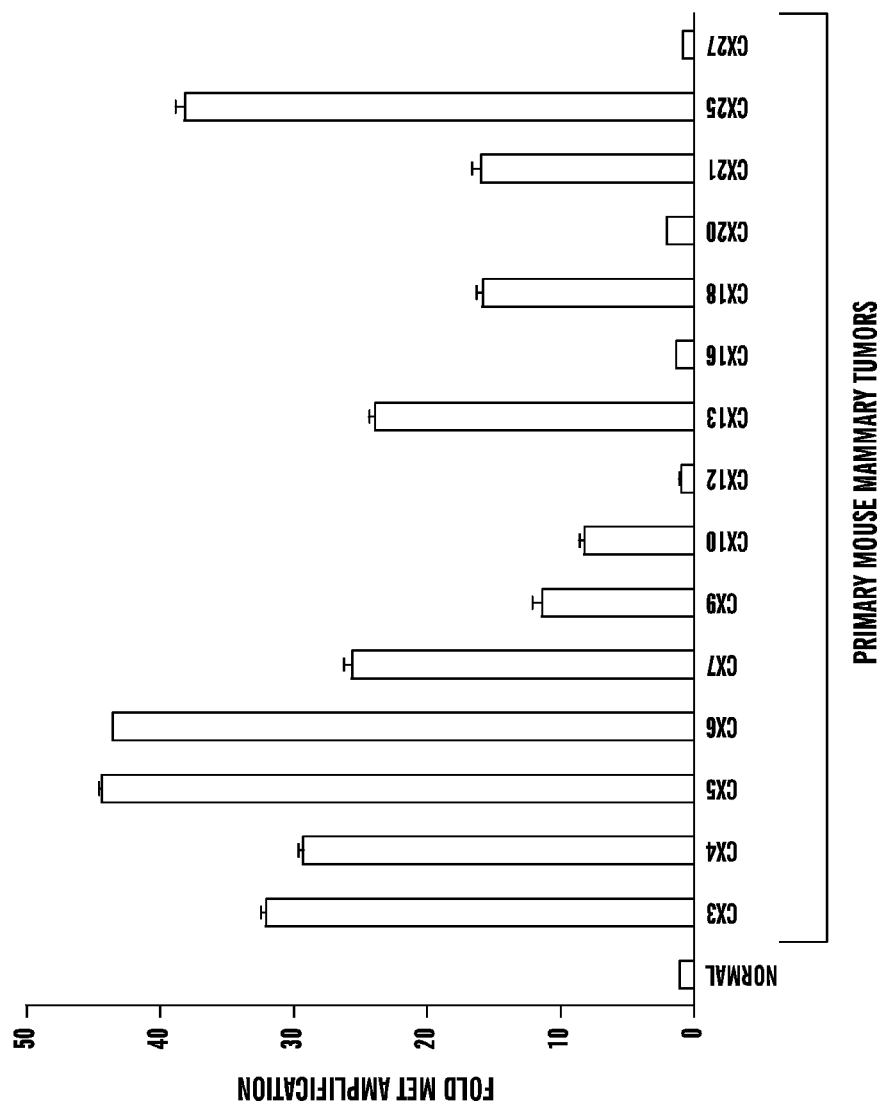
(FIG. 1C) Independent confirmation of MET amplification using qPCR. Fold amplification represents the ratio of Met signal (top of chromosome 6) to control, Edem1, a gene that is genomically stable based on the microarray analysis of all 15 tumors (middle of chromosome 6).

10-50 fold amplification of Met was confirmed using quantitative real-time PCR (qPCR) (FIG. 1C). MET encodes a transmembrane tyrosine kinase receptor for Hepatocyte Growth Factor (HGF, scatter factor), which transduces signals implicated in proliferation, migration and morphogenesis (6-8). Ectopic expression of MET, as well as HGF, confers a tumorigenic and metastatic phenotype in cancer-derived cell lines (9-11), and activating mutations have been reported in both sporadic and inherited forms of renal papillary carcinomas (12). Mutations in MET are rare in breast cancer (13, 14), but tumors with high protein expression appear to have a worse clinical prognosis (15, 16). Furthermore, increased HGF/MET signaling can serve as an initiating event for tumorigenesis, as mice overexpressing either HGF or mutant Met in mammary epithelium develop breast tumors (17-19).

Figure 1E:
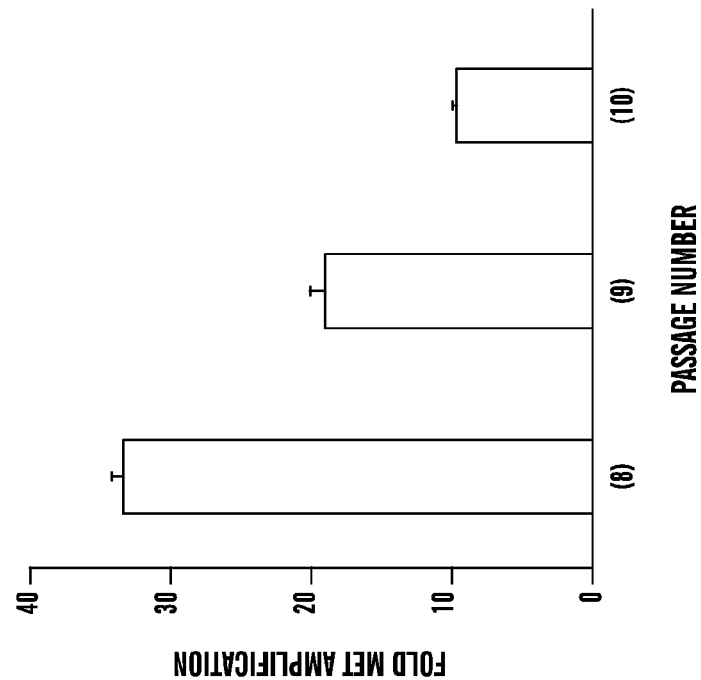
(FIG. 1E) Loss of unstable Met amplification in tumor-derived low passage Brca1$^{\Delta 11/co}$ Trp53$^{+/-}$ MMTV-Cre cells as a function of passage number in culture. Met gene copy number was quantified by qPCR.
Figure 1D:
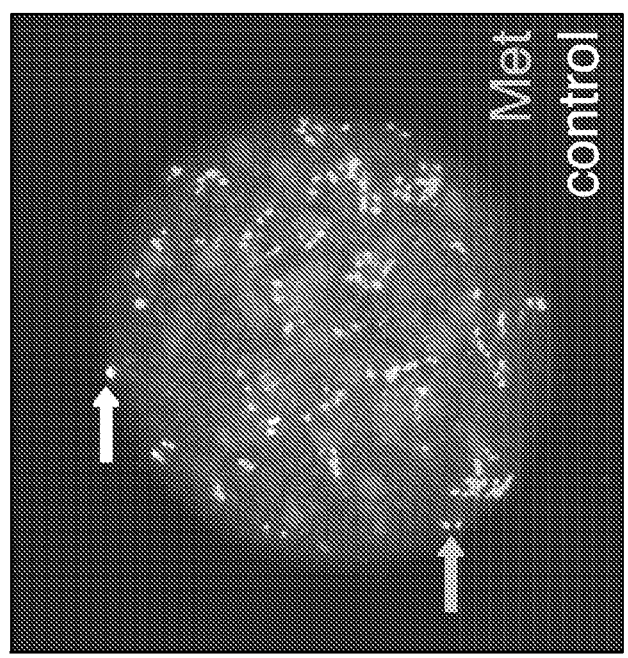
(FIG. 1D) Representative FISH image of low-passage cells derived from a Brca1$^{\Delta 11/co}$ Trp53$^{+/-}$ MMTV-Cre mammary tumor: Met locus (top of chromosome 6) is shown in red and control probe (bottom of chromosome 6) is shown in green. Arrows indicate positions of individual loci. Amplified Met gene copies are carried on characteristic "double minute" extrachromosomal elements.
Figure 5:
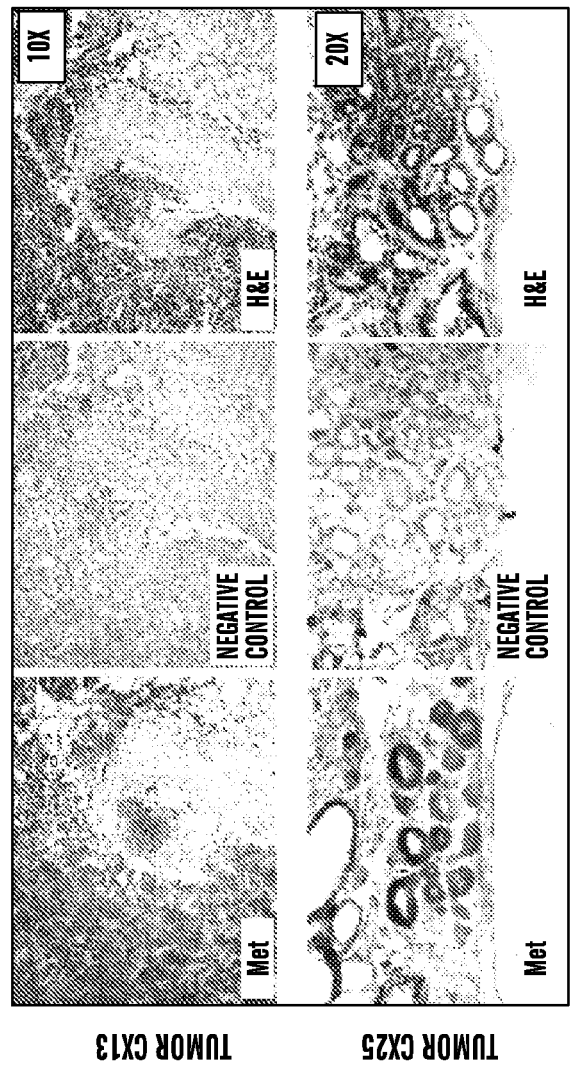
FIG. 5: Met protein is strongly expressed in the primary Brca1^{Δ11/co} Trp53^{+/−} MMTV-Cre tumors bearing Met amplification. Individual tumors (CX13 and CX25) were stained with anti-Met antibody at 1:100 dilution. In slides labeled "negative control" primary antibody against Met was not added during the staining procedure. Diverse histological appearance of Brca1^{Δ11/co} Trp53^{+/−} MMTV-Cre tumors has been previously noted (2).
Figure 6:
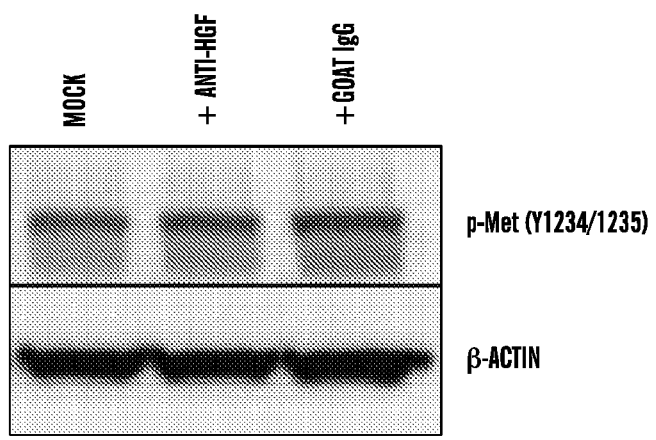
FIG. 6: Activation of MET receptor in Amp+ cells is ligand-independent. Treatment of Amp+ cells with neutralizing anti-HGF antibody (3-5) does not affect MET activation. Cells were serum starved for 24 h and subsequently treated with 1 μg/ml anti-HGF antibody or goat IgG control in serum-free media for another 24 h. Cells were harvested and MET phosphorylation status was measured by immunoblotting (β-actin loading control).

No mutations were present in the coding sequence of amplified Met from any of the mammary tumors of Brca1$^{\Delta 11/co}$ Trp53$^{+/-}$ MMTV-Cre mice, suggesting that overexpression of the wild type receptor is sufficient to confer a selective advantage in tumor cells with this genetic background. Consistent with the presence of DNA amplification, the primary tumors expressed high levels of Met protein (FIG. 5). Fluorescent In Situ Hybridization (FISH) analysis of early passage cell lines derived from these tumors showed that the amplified Met genes are carried on "double minute" extrachromosomal elements (FIG. 1D). While amplification of Met appears to be common in this mouse model of Brca1/p53-driven mammary tumorigenesis, the amplified gene copies are rapidly lost upon establishment of cell lines, presumably reflecting the absence of selection pressure under in vitro culture conditions (FIG. 1E).

Amplification of Met was not observed in other common mouse models of mammary carcinogenesis, including MMTV-driven Erbb2 and c-Myc (data not shown), suggesting that the initiating Brca1/p53 lesion in our mouse tumor model may dictate subsequent secondary genetic lesions. In humans, overexpression of the receptor has been reported in many epithelial cancers, but gene amplification in breast cancer has not been systematically analyzed. To extend our findings from the mouse model, we tested a panel of 100 primary human breast cancers. While about 10% of cases had increased MET gene copy number (3-6 copies), no high level Met amplification was found (data not shown). Similarly, no cases of BRCA1- or BRCA2-linked breast tumors (0/9) or breast cancers from patients with TP53-mutant Li-Fraumeni syndrome (0/13) displayed elevated MET gene copy numbers (data not shown). MET amplification therefore is not a common characteristic of human breast cancer.

Figure 2A:
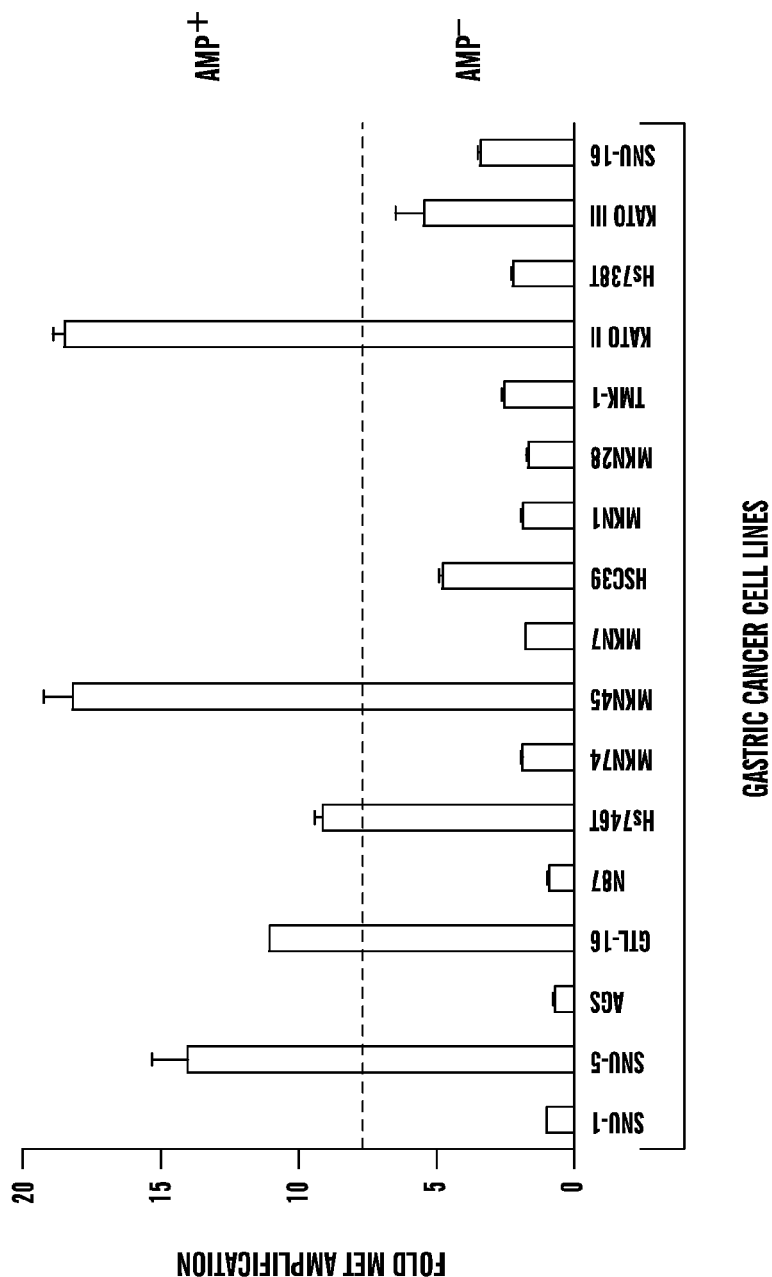
(FIG. 2A) Human gastric cell lines screened for the presence of MET amplification using qPCR. The relative MET copy number is derived by comparison with an unrelated control locus, TOP3A. The horizontal red line separates cells with >8-fold MET amplification (Amp$^+$) from cells with no or low level MET amplification (Amp$^-$).
Figure 2B:
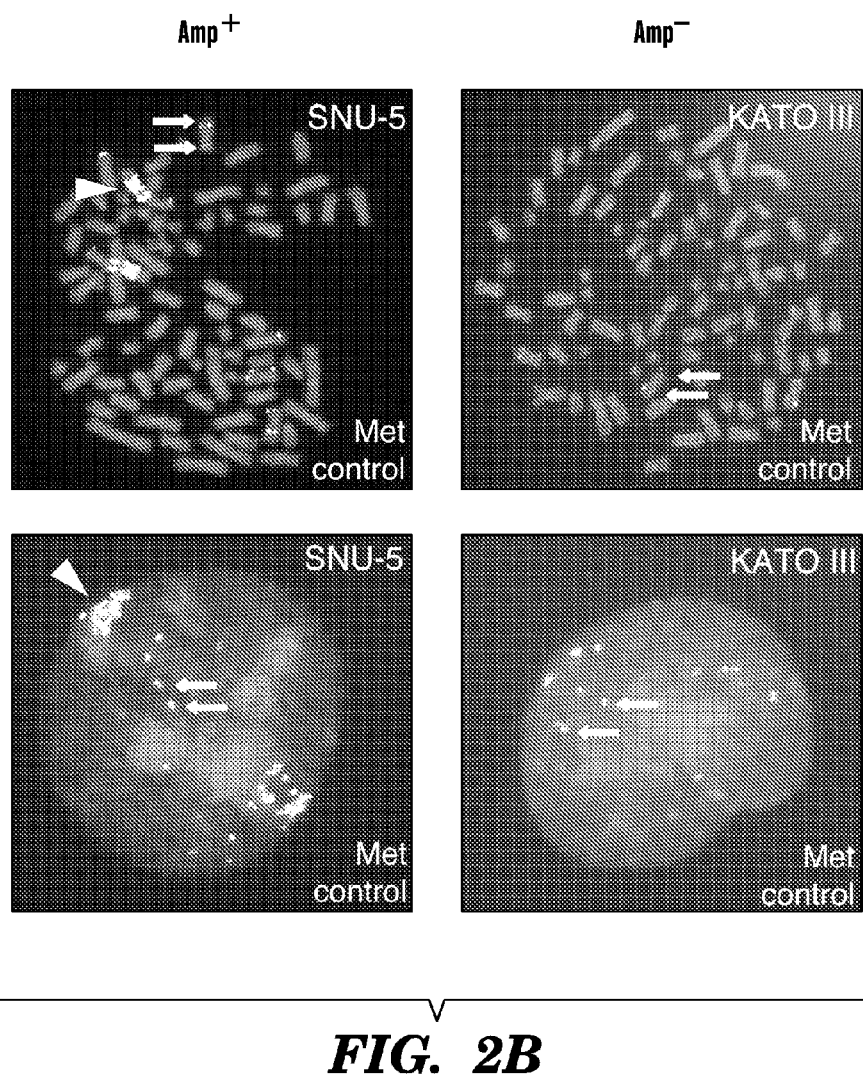
(FIG. 2B) Representative metaphase (upper panel) and interphase (lower panel) FISH analysis of human gastric cancer cell lines showing amplification of MET within characteristic homogeneously staining regions (HSRs) in Amp$^+$ cells. In SNU-5 cells (Amp$^+$) with high level amplification, the MET signal (red) is present in HSRs (red arrowhead) that are distinct from the endogenous gene locus (7q31 region, red arrow). Control probe on the opposite arm of chromosome 7 (7p21 region) is shown in green (green arrow). In KATO III cells with <8-fold MET amplification (Amp), the increased gene copy number is associated with individual chromosomal fragments (aneuploidy).

In contrast, MET amplification has been reported in 10-20% of all primary gastric cancers, including up to 40% in the scirrhous histological subtype (20, 21). Indeed, we found increased MET gene copy numbers in 5/17 (29%) gastric cell lines tested (FIG. 2A). In all these cell lines, the amplified gene copies were stably integrated within a characteristic homogeneously staining region (HSR) of chromosomes (FIG. 2B). No mutations were present in the coding sequence of MET in any of the gastric cancer cell lines, making it possible to test the contribution of wild type MET amplification to cellular proliferation and survival.

Figures 3A, 3B:
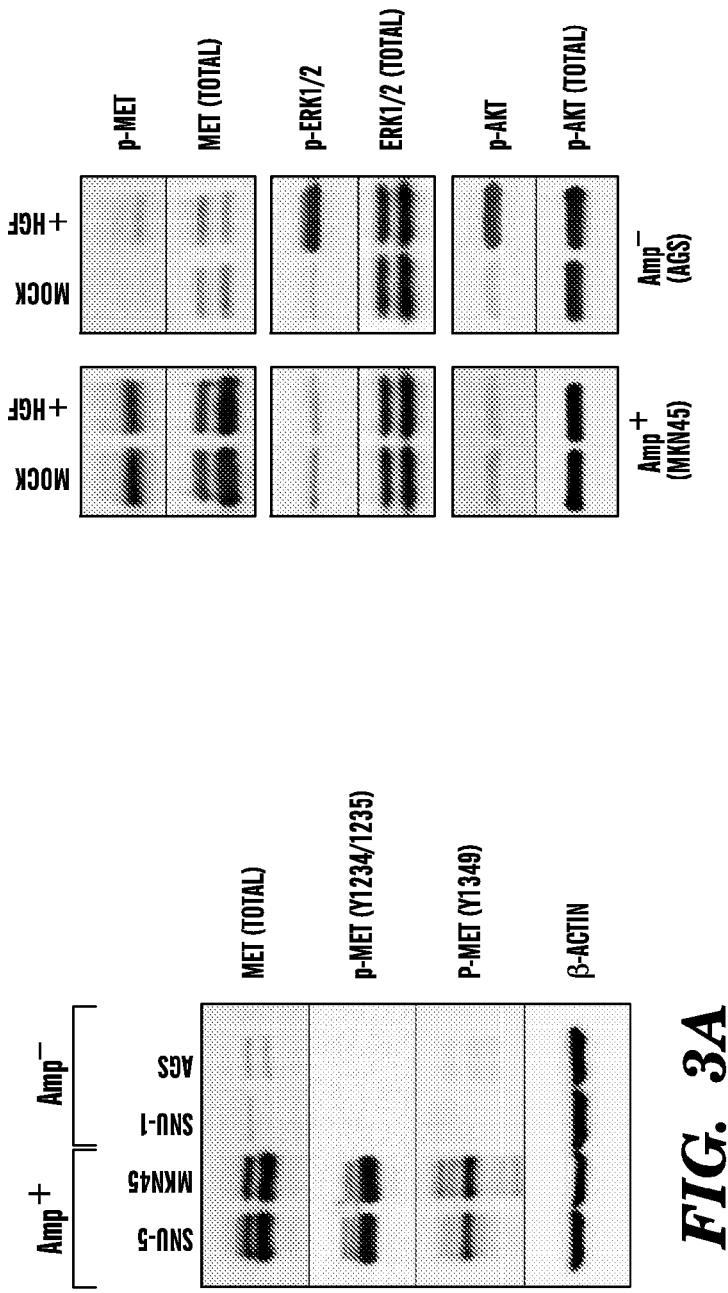
(FIG. 3A) MET is constitutively activated in the Amp$^+$ cells. Immunoblotting analysis demonstrating high levels of MET protein expression in two representative Amp$^+$ cell lines, compared with two Amp$^-$ cell lines. Immunoblotting using two phospho-specific MET antibodies (against Y1234/1235 and against Y1349) shows strong phosphorylation of the receptor only in Amp$^+$ cells (β-actin loading control).
(FIG. 3B) Effect of HGF on MET activation in Amp$^+$ and Amp$^-$ cells (representative immunoblots). Cells were serum-starved for 24 h and treated with 40 ng/ml HGF for 10 minutes. Phosphorylation of MET (Y1234/1235) is unaltered in Amp$^+$ cells treated with HGF, but it is induced by HGF in Amp$^-$ cells (total MET control). Phosphorylation of the downstream effectors ERK1/2 (T202/Y204), and AKT (S473) is also unaltered by HGF treatment in Amp$^+$ cells, but strongly induced in Amp$^-$ cells treated with HGF.
Figure 3C:
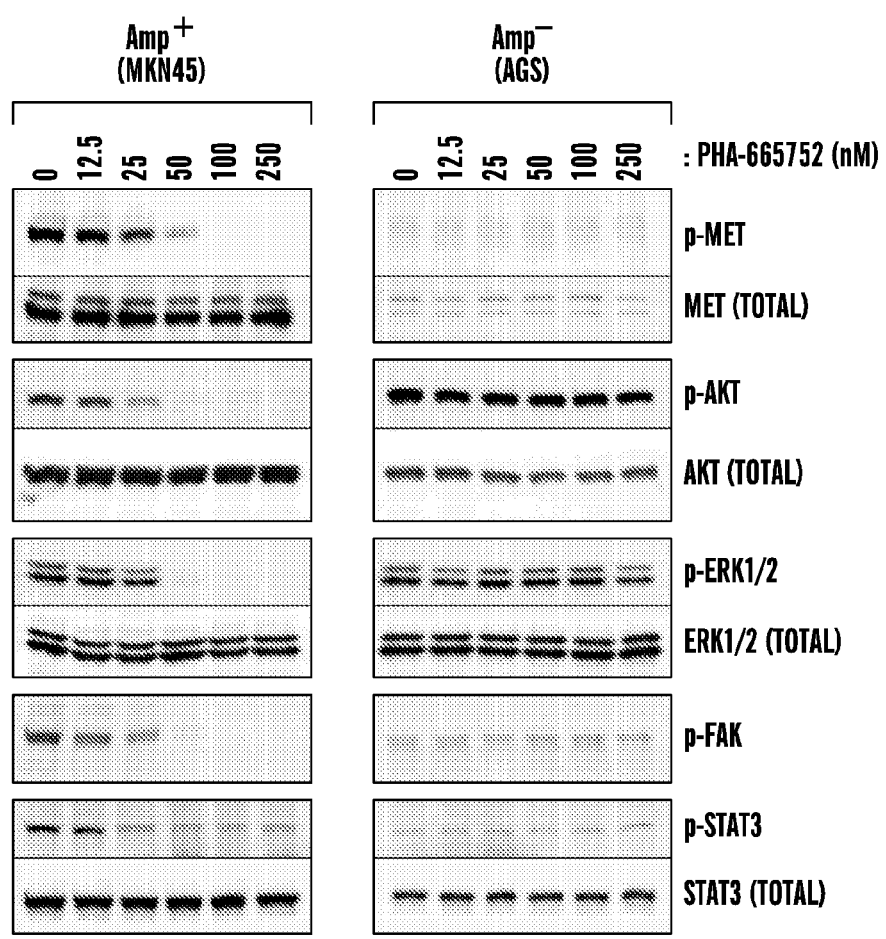
(FIG. 3C) Inhibition by PHA-665752 of MET autophosphorylation and activation of downstream effectors ERK1/2, AKT, STAT3, and FAK in Amp$^+$ cells, but not in Amp cells. Cells were treated with increasing concentrations of PHA-665752 for 3 hours prior to analysis. Inhibition of MET by PHA-665752 suppresses constitutive phosphorylation of these effectors in Amp$^+$ cells, but Amp cells are unaffected (representative blots shown).

Five gastric cancer cell lines with >8-fold MET amplification (Amp$^+$) were compared with 12 cell lines without amplification (Amp$^-$). As expected, Amp$^+$ cells had a dramatic elevation in MET protein expression. Remarkably, these cells also displayed constitutive MET phosphorylation (FIG. 3A), which was not further enhanced by treatment with its ligand HGF (FIG. 3B). In contrast, Amp$^-$ cells had low or undetectable levels of MET phosphorylation under standard culture conditions, but demonstrated phosphorylation of the receptor following treatment with HGF. Consistent with the ligand-independence of MET activation in Amp$^+$ cells, no HGF mRNA expression was detectable by quantitative RT-PCR in 4/5 cell lines (Table 3) and treatment with neutralizing anti-HGF antibody did not affect the levels of MET phosphorylation (FIG. 4). Constitutive activation of the receptor may therefore result from the very high level of protein expressed, an effect that has been reported for MET (22) and other receptor tyrosine kinases (23).

To test the potential therapeutic relevance of these observations, we made use of a highly specific MET kinase inhibitor, PHA-665752 (24) (Pfizer). This drug effectively suppressed the constitutive MET autophosphorylation in Amp$^+$ cells. Furthermore, treatment with PHA-665752 also abrogated the baseline phosphorylation of downstream effectors of growth factor receptors, ERK1/2, AKT, STAT3, and FAK in these cells (FIG. 3B). Thus, constitutive activation of these proliferative and survival pathways in Amp+ cells appears to be dependent upon MET signaling.

Figure 4A:
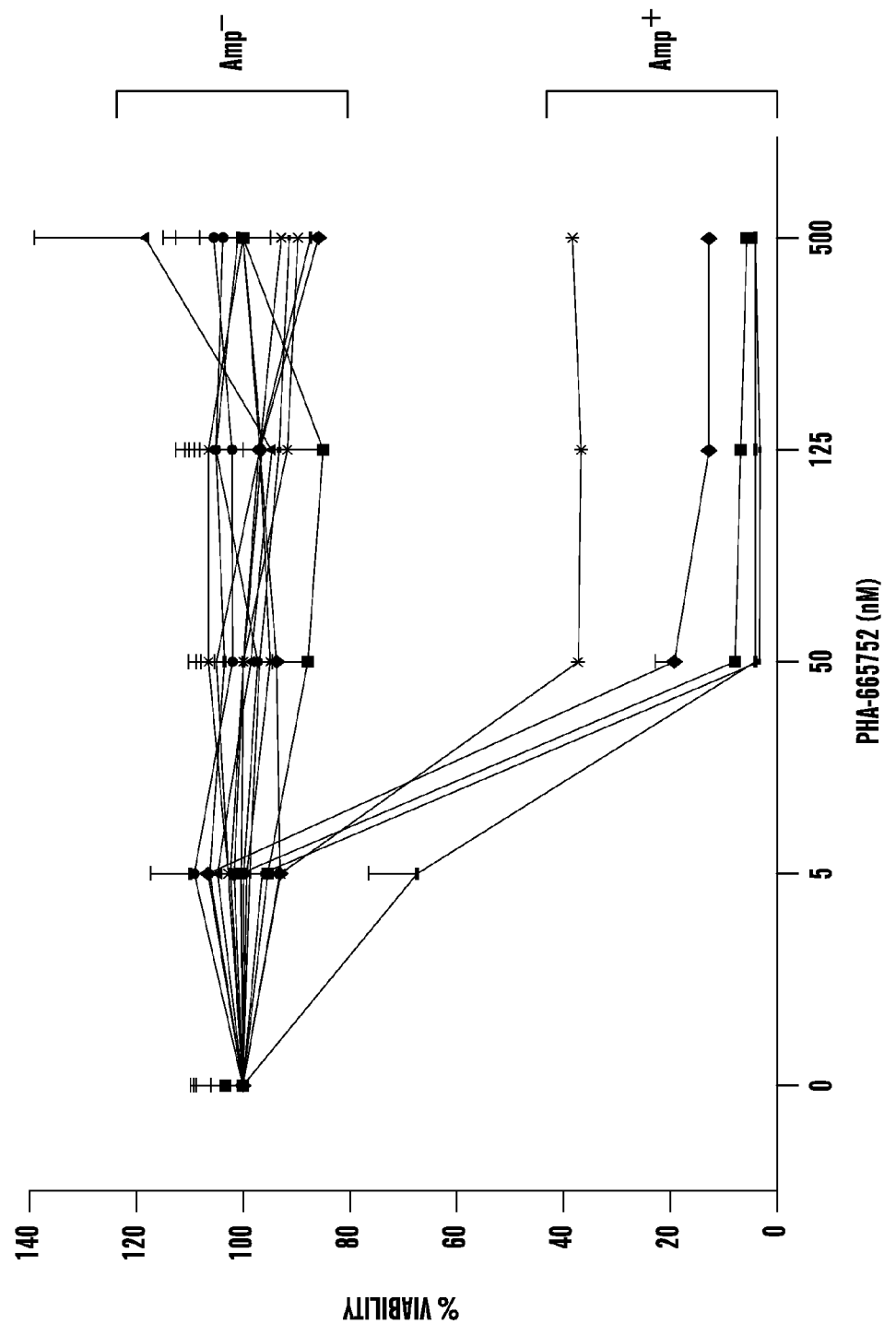
(FIG. 4A) Amp$^+$ cells (red) show dramatically increased sensitivity to PHA-665752, relative to Amp$^-$ cells (black). Cells were grown for 96 hours in the presence of increasing PHA-665752 concentration and their viability was assessed using MTT assays. Results are plotted as a percentage of viability of untreated cells.
Figure 4C:
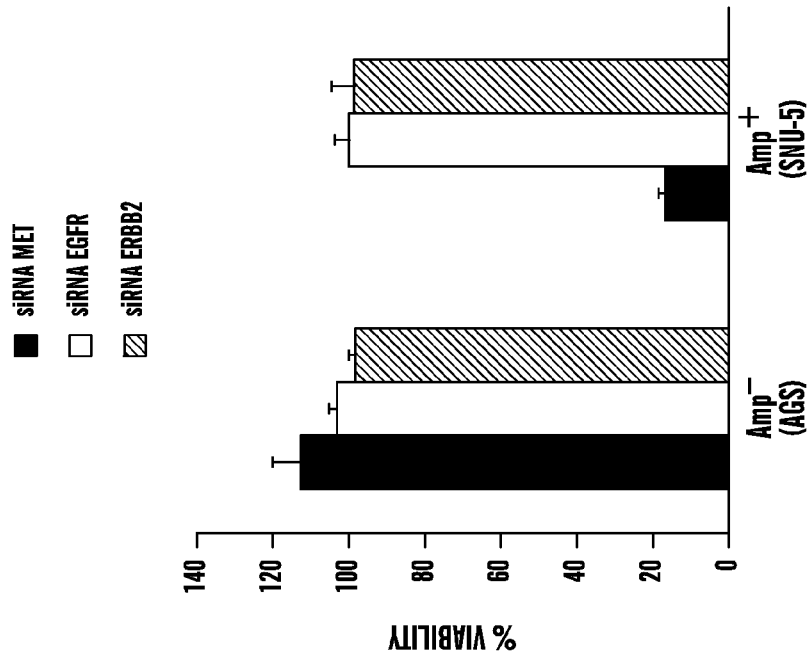
(FIG. 4C) Selective killing of Amp$^+$ cells following siRNA-mediated knockdown of MET. Viability in Amp$^+$ and Amp$^-$ cells was compared 96 hours after knockdown of MET or of unrelated receptors (EGFR and ERBB2). Cell viability was measured using the MTT assay and plotted as a percent of cells treated with a nonspecific (control) siRNA duplex.
Figure 4B:
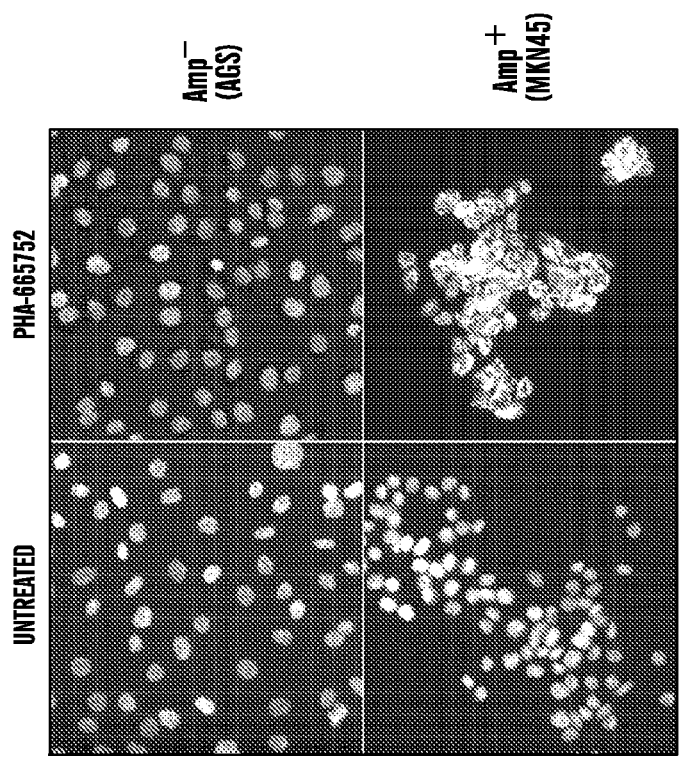
(FIG. 4B) Induction of apoptosis following treatment of Amp$^+$ cells with PHA-665752. Amp$^+$ and Amp$^-$ cells were treated with PHA-665752 for 72 hours, and induction of apoptosis was monitored by immunofluorescent staining of fixed cells with an antibody specific for cleaved caspase-3 (green). Cells were co-stained with DAPI to show nuclei.

In contrast, in Amp cells where MET is not constitutively autophosphorylated, PHA-665752 had no effect on baseline phosphorylation of ERK1/2, AKT, STAT3 or FAK, indicating that these effectors are likely to be activated through alternative growth factor receptors. In 5/5 Amp+ cells, continued treatment with PHA-665752 led to a dramatic decrease in the number of viable cells (FIG. 4A, Table 4), accompanied by the induction of apoptosis (FIG. 4B). In contrast, 12/12 Amp− cells were resistant to the MET kinase inhibitor, showing no change in their proliferation rate following drug treatment (p=0.00016, Fisher's Exact Test, two-sided).

Figure 4D:
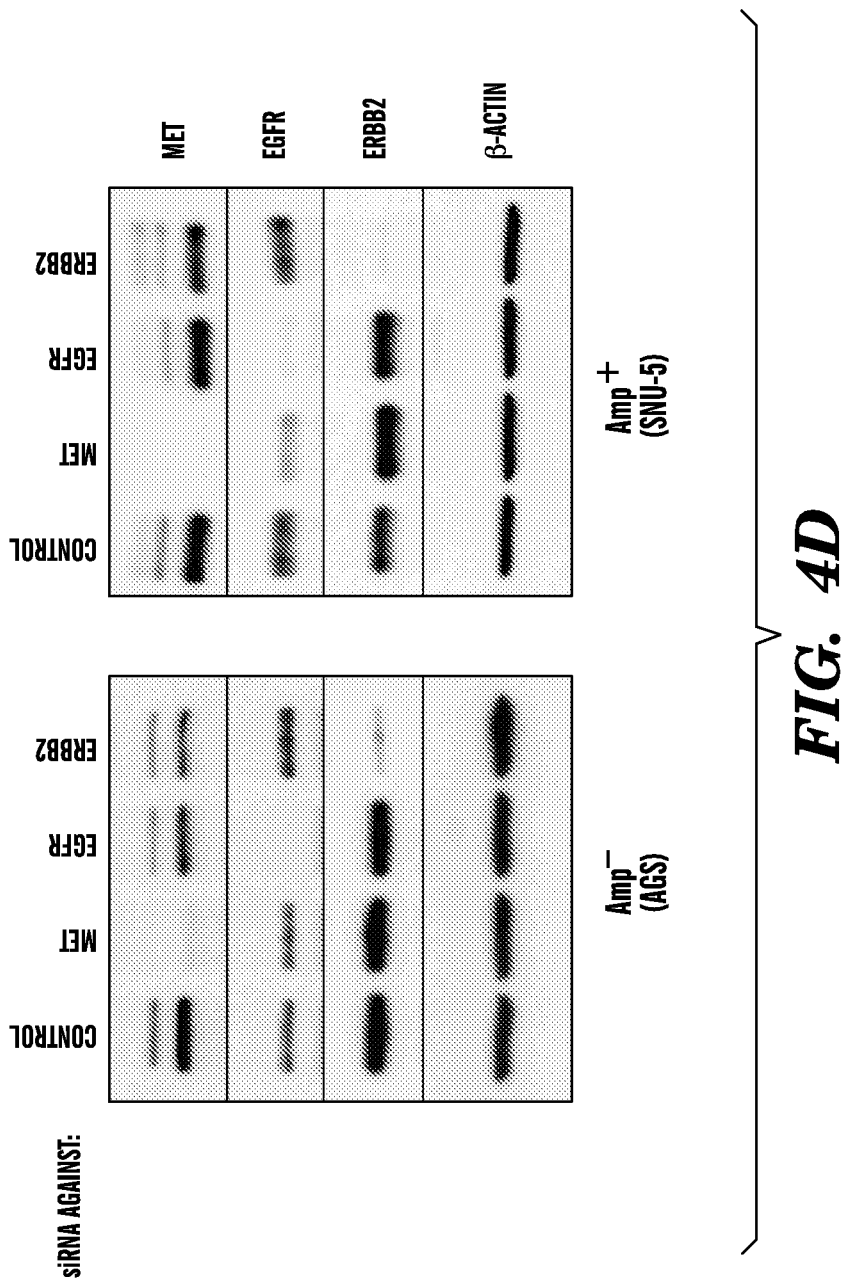
(FIG. 4D) Effective knockdown of targeted receptor tyrosine kinases using siRNAs. Representative Amp$^+$ and Amp$^-$ cells were treated with indicated siRNAs and protein levels were monitored 48 h later by immunoblotting (β-actin loading control).

To confirm that the differential effects of PHA-665752 are truly attributable to its effect on MET, we treated cells with siRNA targeting the MET receptor. Consistent with the drug studies, a marked reduction in cell viability was evident in Amp+ cells following MET knockdown, whereas no such effect was observed in Amp− cells (FIGS. 4C, 4D). Amp+ cells were not affected by knockdown of other receptors, such as epidermal growth factor receptor (EGFR) or ERBB2. Thus, a subset of gastric cancer cell lines defined by >8-fold MET amplification appears to be dependent upon constitutive activation of this growth factor receptor for their survival and show exquisite sensitivity to the tyrosine kinase inhibitor PHA-665752.

Analysis of the role of MET in malignancy has largely focused on its effect in promoting cell motility, invasion and metastasis, rather than its primary transforming potential. However, the ability of MET itself to drive malignant proliferation is evident from its central role in initiating human papillary renal carcinoma (12), and in a number of mouse models with ectopic expression of the activated receptor (17-19). Our observations suggest that even in human cancers where MET alteration may or may not be the initiating genetic event, amplification of the receptor leads to a dependence on its transduced signals (i.e. oncogene addiction (1), thereby identifying a marker of drug response.

As such, MET amplification in gastric and other types of cancers may constitute a molecular marker for targeted therapy, analogous to the BCR-ABL translocation in chronic myeloid leukemia (CML) (27, 28), and activating kinase mutations within c-KIT in gastrointestinal stromal tumors (GIST) (29, 30) and within the epidermal growth factor receptor (EGFR) in non-small cell lung cancer (NSCLC) (31, 32). While our studies focused on cell lines with stable MET amplification on HSRs, tumors with unstable amplification subject to in vivo selection pressures may also prove responsive to MET inhibition. As MET inhibitors enter clinical trials in the near future, our observations highlight an approach in which preclinical studies defining molecular markers of drug susceptibility may help select subsets of cancers most likely to demonstrate a clinical response to such targeted inhibitors.

Materials and Methods:

Microarray Screening

Tumors derived from the Brca1$^{\Delta11/co}$ Trp53$^{+/-}$ A MMTV-Cre animals were histologically analyzed to be over 90% pure. DNA from was extracted from matching pairs of tumor and liver (normal control) of the same animal and processed for microarray analysis as described before (33).

Quantitative Real-Time PCR

The sequences of the PCR primer pairs and fluorogenic MGB probes (all listed from 5' to 3') used for DNA copy number analyses:

| | | |
|---|---|---|
| Hs.MET_F, | TGTTGCCAAGCTGTATTCTGTTTAC | (SEQ ID NO 1) |
| Hs.MET_R, | TCTCTGAATTAGAGCGATGTTGACA | (SEQ ID NO 2) |
| Hs.MET_probe, | VIC-TGGATAATTGTGTCTTTCTCTAG-MGBNFQ | (SEQ ID NO 3) |
| Hs.TOP3A_F, | CCACTGCGAACTTAAGAAAACTTTG | (SEQ ID NO 4) |
| Hs.TOP3A_R, | TTCTCTATCACAGTCAGTCCAGATCA | (SEQ ID NO 5) |
| Hs.TOP3A_probe, | VIC-AACGAGAGACTCGCCAGT-MGBNFQ | (SEQ ID NO 6) |
| Mm.Met_F, | TTCCAACCCTCTTTGATTGCA | (SEQ ID NO 7) |
| Mm.Met_R, | GCTACTTGAAGGCCAAATCCTATAA | (SEQ ID NO 8) |
| Mm.Met_probe, | VIC-AATCCAACTGTGAAAGAT-MGBNFQ | (SEQ ID NO 9) |
| Mm.Edem_F, | GTTTCCACACCACCTTTGATTCT | (SEQ ID NO 10) |
| Mm.Edem_R, | GTCAGGAGGAACACCTGTCTTCA | (SEQ ID NO 11) |
| Mm.Edem_probe, | VIC-CCCACTGCAGGTGAA-MGBNFQ | (SEQ ID NO 12) |

All samples were done in triplicates and the relative MET copy number was derived by standardizing the input DNA to the control signal (TOP3A for the human samples and Edem1 for the mouse samples).

The sequences of the PCR primer pairs and fluorogenic MGB probes (all listed from 5' to 3') used for quantitating relative HGF expression levels are:

| | | |
|---|---|---|
| Hs.HGF_F, | CGCTACGAAGTCTGTGACATTCC | (SEQ ID NO 13) |
| Hs.HGF_R, | CCCATTGCAGGTCATGCAT | (SEQ ID NO 14) |
| Hs.HGF_probe, | VIC-CAGTGTTCAGAAGTTG-MGBNFQ | (SEQ ID NO 15) |
| Hs.GAPDH_F, | GGTGGTCTCCTCTGACTTCAACA | (SEQ ID NO 16) |
| Hs.GAPDH_R, | GTGGTCGTTGAGGGCAATG | (SEQ ID NO 17) |
| Hs.GAPDH_probe, | VIC-AACCACTCCTCCACCTTTGACGCTG-TAMRA | (SEQ ID NO 18) |

All samples were done in triplicates and the relative HGF expression levels was derived by dividing the HGF signal by the GAPDH signal. All values are relative to the lowest expressing cell line, which was assigned an arbitrary expression value of 1.

Mutational Screening

DNA isolated from fresh frozen tissue or cultured cell lines was amplified by direct PCR amplification or nested PCR amplification. Genomic was amplified in a 25 ul reaction consisting of 1× buffer, 50 uM dNTP, 200 nM sense primer, 200 nM antisense primer and 0.8 U Expand Taq (Roche Diagnostics, Germany). Primer sequences and annealing temperatures are provided in the table below. PCR amplicons were purified using exonuclease I (United States Biochemical, Cleveland, Ohio) and shrimp alkaline phosphatase (United States Biochemical, Cleveland, Ohio) and diluted in water prior to sequencing. Bidirectional capillary sequencing was performed using BigDye Terminator v1.1 chemistry (Applied Biosystems, Foster City, Calif.) in combination with an ABI3100 instrument. Internal sequencing primers for exons 4 and 5 of human MET were (exon 4:

(exon 4:
CCACAAGCCCTGCTAATCTGTTATT    (SEQ ID NO 19)
and

CTTTCTTGGAGAACAAATTAACTAG    (SEQ ID NO 20))
and (exon 5:
CACCGTTATGACAGGATTTGCACAC    (SEQ ID NO 21)
and

GCTGATGACTCACAGCTAAATGAG.    (SEQ ID NO 22))

Electropherograms were aligned and reviewed using Sequence Navigator software in combination with Factura.

TABLE 1 primers and annealing temperatures used for human MET sequencing.

|  | PRIMER SEQUENCE (Sense) | PRIMER SEQUENCE (Anti-Sense) | Annealing temp. °C. |
|---|---|---|---|
| Primary Primer | | | |
| Exon 2A | GTCATGTCCAACCGGACAATGCATC (SEQ ID NO 23) | CCAGTCTTGTACTCAGCAACCTTC (SEQ ID NO 24) | 52 |
| Exon 2B | GTCATTCTACATGAGCATCACATT (SEQ ID NO 25) | CTGATATCGAATGCAATGGATGATC (SEQ ID NO 26) | 50 |
| Exon 2C | CAGTGTCCTGACTGTGTGGTGAGCG (SEQ ID NO 27) | GCTTGCTGACATACGCAGCCTGAAG (SEQ ID NO 28) | 58 |
| Exon 2D | GGAAATGCCTCTGGAGTGTATTCTC (SEQ ID NO 29) | GGTGTAAATGAAGATTCAATTCCTC (SEQ ID NO 30) | 52 |
| Exon 3 | CCTTGCCATTATCCTCCAGGCTCTG (SEQ ID NO 31) | CAGAAAGTAGACCAGGCTTCATTG (SEQ ID NO 32) | 58 |
| Exon 4 & 5 | CCACAAGCCCTGCTAATCTGTTATT (SEQ ID NO 33) | GCTGATGACTCACAGCTAAATGAG (SEQ ID NO 34) | 58 |
| Exon 6 | CTTGTTTCATTAACATGTCATGTAG (SEQ ID NO 35) | TTCAAGAGATGAGCTTCTTGAGCAA (SEQ ID NO 36) | 58 |
| Exon 7 & 8 | GTCAGCTCACCATTTAGAGTTAATG (SEQ ID NO 37) | GGTACAGATATTAATTCAAATTGAC (SEQ ID NO 38) | 58 |
| Exon 9 | GATCCAGTCAGATTAAACAGCCTAC (SEQ ID NO 39) | CAACATAACAGCATCAAAGCCAGAG (SEQ ID NO 40) | 58 |
| Exon 10 | AAGTTGTTTCCAAAGAACAGTTACC (SEQ ID NO 41) | CTACACTGCAAGGAAATTAACTAGC (SEQ ID NO 42) | 58 |
| Exon 11 | TGTGTAGTCTAACATTAGGAAGTTA (SEQ ID NO 43) | GTATAAGATACAATGGCCAAGTAC (SEQ ID NO 44) | 52 |
| Exon 12 | GTATCATAGAATCGTGTGCCTTGGC (SEQ ID NO 45) | CTAGGAATGCAGGCTGAGTTGATG (SEQ ID NO 46) | 58 |
| Exon 13 | GAAGGCAGTTATGCCATTTGTAGAA (SEQ ID NO 47) | CATCGTAGCGAACTAATTCACTG (SEQ ID NO 48) | 58 |
| Exon 14 | CCTTAAGAACACAGTCATTACAG (SEQ ID NO 49) | GTGTCAAATACTTACTTGGCAGAGG (SEQ ID NO 50) | 58 |
| Exon 15 | GCTTTCAAAATTAATACTTAGTCTAC (SEQ ID NO 51) | CTTGTTATCACTGCTCTGTCAGTTG (SEQ ID NO 52) | 58 |
| Exon 16 | GTACTCTTTTGCTGTATAGAAAG (SEQ ID NO 53) | CCACAAGGGGAAAGTGTAAATCAAC (SEQ ID NO 54) | 58 |
| Exon 17 | CAAGATGCTAACTGTGTGGTTTACC (SEQ ID NO 55) | GAGGTGCATTTGAATGATGCTAAC (SEQ ID NO 56) | 58 |
| Exon 18 | GACCAAACTAATTTTTGAGACAAG (SEQ ID NO 57) | CACATCGATTTAAGATTGTAACAG (SEQ ID NO 58) | 58 |
| Exon 19 | CTTCCTTCAGAAGTTATGGATTTC (SEQ ID NO 59) | GAAGAAAACTGGAATTGGTGGTGTTG (SEQ ID NO 60) | 58 |

TABLE 1-continued primers and annealing temperatures used for human MET sequencing.

| | PRIMER SEQUENCE (Sense) | PRIMER SEQUENCE (Anti-Sense) | Annealing temp. ° C. |
|---|---|---|---|
| Exon 20 | CAGAAAGCGTATTGAGTATGTAAAGC (SEQ ID NO 61) | GCATTTTAGCATTACTTCATATCTG (SEQ ID NO 62) | 58 |
| Exon 21 | GAAGACTCCTACAACCCGAATACTG (SEQ ID NO 63) | CAAGTCCTATAATAGTGCAATTTTG (SEQ ID NO 64) | 58 |
| Secondary Primer | | | |
| Exon 14 | GAACACAGTCATTACAGTTTAAG (SEQ ID NO 65) | CTTACTTGGCAGAGGTAAATACTTGC (SEQ ID NO 66) | 58 |
| Exon 15 | CTTAGTCTACTTAAATGAAAATCTG (SEQ ID NO 67) | CTGCTCTGTCAGTTGCTTTCACC (SEQ ID NO 68) | 58 |
| Exon 16 | GCTGTATAGAAAGAAGAAAG (SEQ ID NO 69) | CAGTGGTAGCTGATTTTTCCACAAGG (SEQ ID NO 70) | 58 |
| Exon 17 | CTGTGTGGTTTACCATTTCATTGC (SEQ ID NO 71) | GACTCAGAGGAGGCCTATTTTG (SEQ ID NO 72) | 58 |
| Exon 18 | GACCAAACTAATTTTTGAGACAAG (SEQ ID NO 73) | GAAATAAAGGACTTTTGCATAAG (SEQ ID NO 74) | 58 |
| Exon 19 | GTTATGGATTTCAAATACTGAAGC (SEQ ID NO 75) | GTCCATTTTTACATATGAAGAAAAC (SEQ ID NO 76) | 58 |
| Exon 20 | GAGTATGTAAAGCCAAGTTTAG (SEQ ID NO 77) | CATTACTTCATATCTGTTCCAAAAAG (SEQ ID NO 78) | 58 |
| Exon 21 | CTGCCCAGACCCCTTGTAAGTAGTC (SEQ ID NO 79) | GTGCAATTTTGGCAAGAGCAAAG (SEQ ID NO 80) | 58 |

TABLE 2

Table of primers and annealing temperatures used for mouse Met sequencing.

| Primary Primer | PRIMER SEQUENCE (Sense) | PRIMER SEQUENCE (Anti-Sense) | Annealing temp. ° C. |
|---|---|---|---|
| Exon 1A | GATATCGAAGCTGGAGGAGTCATGC (SEQ ID NO 81) | CATAGTATGTGTCAACAAGCAGAG (SEQ ID NO 82) | 58 |
| Exon 1B | GTTGGAACACCCAGATTGTTTACC (SEQ ID NO 83) | CGAAGGCATGTATGTACTTTATGG (SEQ ID NO 84) | 58 |
| Exon 1C | CGGCTGAAGGAAACCCAAGATGG (SEQ ID NO 85) | GACAGACGTTTATTCTGCTTCATAC (SEQ ID NO 86) | 58 |
| Exon 2 | CATGTGACTATCCTTGATATTCTG (SEQ ID NO 87) | GTTACCCCTTTGGGTTCTGTCTCTAG (SEQ ID NO 88) | 58 |
| Exon 3 | CTAACAGGATGCACTGTGGGTCTTC (SEQ ID NO 89) | GGAGGCATGAGTCTAAGTCTCAG (SEQ ID NO 90) | 58 |
| Exon 4 | GATGCTACTCAATTAGATGCCGTG (SEQ ID NO 91) | GATGTCCCCCACGTAGATGAATAC (SEQ ID NO 92) | 58 |
| Exon 5 | CACACACAGGAACACACGCATGTG (SEQ ID NO 93) | CCTGGATGAGCATGTTGAACAATTG (SEQ ID NO 94) | 58 |
| Exons 6 & 7 | CTCACAATTTGGGGTTTAATATCC (SEQ ID NO 95) | GAATCATTAGTGGGAGAGAATCACG (SEQ ID NO 96) | 58 |
| Exon 8 | CTTACAGATGTAATTTTGGAATATG (SEQ ID NO 97) | CACAGCAGCGTTTAAATAAATGAGG (SEQ ID NO 98) | 58 |
| Exon 9 | GCGAGTCCTCTAACATCATAAGAG (SEQ ID NO 99) | GTACCATTTGACCTCTGCTGCAGG (SEQ ID NO 100) | 58 |

TABLE 2-continued

Table of primers and annealing temperatures used for mouse Met sequencing.

| Primary Primer | PRIMER SEQUENCE (Sense) | PRIMER SEQUENCE (Anti-Sense) | Annealing temp. ° C. |
|---|---|---|---|
| Exon 10 | GTGTAACAACTGATGTGTTTTGAG (SEQ ID NO 101) | GTAGAATAGGATACACTGAGCAC (SEQ ID NO 102) | 58 |
| Exon 11 | CAGCGTCTGCATTTGTTGTATTCTTG (SEQ ID NO 103) | GCTAGAGCCAACATACAGATGAGC (SEQ ID NO 104) | 58 |
| Exon 12 | CCACCAGGGTGCTAATTGGAATCC (SEQ ID NO 105) | CTTTTATGAATGCTTATTAGACAAC (SEQ ID NO 106) | 58 |
| Exon 13 | GTTGTCTAATAAGCATTCATAAAAG (SEQ ID NO 107) | CAGGACAAAAAGCAAAAAGCAAG (SEQ ID NO 108) | 58 |
| Exon 14 | GAGTGTTCCCAGCCTAGCATTTCG (SEQ ID NO 109) | CTCGTTATCAGGCTCTGTCAGGAG (SEQ ID NO 110) | 60 |
| Exon 15 | GCATGGAGAGAAGTGTAATGCATC (SEQ ID NO 111) | CCACAAGGGAAAGTGCAAATGAACAC (SEQ ID NO 112) | 60 |
| Exon 16 | TCTCTTGCTACCTAAATTTGAAAAAG (SEQ ID NO 113) | CCTTGTTAAGGGCATTTGCTACTC (SEQ ID NO 114) | 52 |
| Exon 17 | CCACAGGGCATGAGTTATTATTTG (SEQ ID NO 115) | CTTCGAAGAGAAGAGAGAAAATGTC (SEQ ID NO 116) | 60 |
| Exon 18 | CAATAGGCCAGAGGAAATTATGG (SEQ ID NO 117) | GTTACCATACAACTACGGAGAG (SEQ ID NO 118) | 60 |
| Exon 19 | GTGAAGTGTGTCAAGCAAGGATG (SEQ ID NO 119) | CCAGCATTTTAGCATCACTTCGTAC (SEQ ID NO 120) | 58 |
| Exon 20 | CCTTGTAAGTAAGAGTTTGCTGG (SEQ ID NO 121) | GTTAAGTGACCTTCCAAAGGCCAG (SEQ ID NO 122) | 58 |

FISH

Cell lines were grown in the appropriate medium until 70% confluent. Cells were trypsinized, washed in 1×PBS, treated with 0.56% KCl and fixed with 3:1 methanol:acetic acid. Cells were dropped on clean glass slides for interphase and/or metaphase spreads. For FISH in human cells BAC clone CTD-1013N12 containing the full-length MET gene was used. BAC RP11-340A14, mapping to 7q11.2, was used as a control probe. For FISH in mouse cells BAC RP23-173p9 containing the full-length Met gene (6A2 region) was used. BAC RP23-137A12, mapping to 6G3 region, was used as a control probe. All clones were confirmed by PCR using gene-specific or STS markers. Human BAC clones were mapped to normal metaphase spreads to confirm their map positions. BAC DNAs were labeled with Cy3- and FITC-dUTP by nick translation. Metaphase spreads were hybridized with 200 ng of each probe along with 10 ug of Cot-1 DNA in a hybridization buffer containing 50% formamide, 10% dextran sulfate and 2×SSC at 37° C. in a humid chamber for 18-20 hours. Following hybridization slides were washed in 50% formamide/2×SSC pH7.0, and 0.1×SSC solutions at 50° C. Slides were then counterstained with DAPI in antifade solution. Image analysis was performed using the Magnafire software.

Cell Lines

Human gastric cell lines were either purchased from ATCC or were generously donated by Dr. Kay Huebner and Dr. Reuben Lotan. All lines were propagated in RPMI1640 medium supplemented with 10% fetal bovine serum, 2 mM L-glutamine, 50 U/ml penicillin/streptomycin and maintained at 5% $CO_2$ at 37° C.

Immunoblotting

Cells were either directly lysated in 2× sample buffer or in RIPA buffer (150 mM NaCl, 50 mM Tris pH 8.0, 1% NP40, 0.5% DOC, 0.1% SDS, 1 mM EDTA, 10 mM NaF, 1 mM Na-orthovanadate, 1× protease inhibitor cocktail (Roche; Indianapolis, Ind.)). Cell lysates were sonicated for 10 sec and cleared by centrifugation at 14,000 rpm for 10 min at 4° C. Cleared lysates were boiled in sample buffer and loaded onto 10% SDS-PAGE gel. For immunoblotting analysis, proteins were transferred onto Immobilon PVDF membrane (Millipore; Bedford, Mass.) and visualized with Western Lightning Plus chemiluminescence kit (Perkin Elmer; Boston, Mass.).

Antibodies

The phospho-MET (Y1234/Y1235), phospho-AKT (S473), phospho-ERK1/2(T202/Y204), phospho-FAK (Y576/Y577), phospho-STAT3 (Y747), AKT, ERK1/2, STAT3, ERBB2, EGFR, and cleaved caspase-3 antibodies were from Cell Signaling (Beverly, Mass.). The phospho-MET (Y1349) antibody was from Biosource (Camarillo, Calif.). The human MET antibody (C-12) and mouse Met antibody (SP260) were from Santa Cruz Biotechnology (Santa Cruz, Calif.). The β-actin antibody was from Abcam (Cambridge, Mass.). The neutralizing HGF antibody was from R&D Systems (Minneapolis, Minn.). All immunoblots were done with 1:1000 antibody dilution, except for the β-actin antibody, which was used at 1:10000 dilution.

Apoptosis Induction Assay

Cells were plated on coverslips in 12-well dishes and grown to approximately 75% confluency in 10% serum. Subsequently, media was changed to 2% serum and 1 μM PHA- 665752. After 72 h the cells were fixed with 4% paraformaldehyde for 20 minutes. Permeabilization with 1% NP40 for 5 minutes was followed by blocking with 3% BSA for 30 minutes. The coverslips were then incubated overnight at 4° C. with cleaved caspase-3 antibody at 1:200 dilution. The next day, the coverslips were washed 3 times with PBS and incubated with a secondary antibody (goat anti-rabbit FITC-conjugated) for 1 h at 1:250 dilution. Following 5 washes with PBS, coverslips were mounted in Vectashield mounting medium containing DAPI (Vector Laboratories; Burlingame, Calif.).

Viability Assays

Cells were plated in 96-well plate in medium containing 4% fetal bovine serum at approximately 4000 cells/well. The next day the cells were treated with increasing concentrations of PHA-665752. Cell viability was measured 96 h later using the MTT assay. Briefly, 10 ul of 5 mg/ml MTT (Thiazolyl blue) solution was added to each well and incubated for about 2 hours at 37° C. For adherent cell lines, the media was removed from each well and the resultant MTT formazan was solubilized in 100 ul of DMSO. For suspension cell lines, the MMT formazan was solubilized by direct addition of 100 ul of acidic isopropanol (0.1N HCl) to each well. The results were quantitated spectrophotometrically using a test wavelength of 570 nm and a reference wavelength of 630 nm.

RNA

RNA was extracted from cultured cells using RNeasy kit from Qiagen (Valencia, Calif.). c-DNA synthesis was performed using SuperScript II Reverse Transcriptase from Invitrogen (Carlsbad, Calif.).

siRNA-Mediated "Knockdown" of Met Expression

The duplexes targeting MET, EGFR, and ERBB2 were custom SMARTpool mixtures from Dharmacon (Lafayette, Colo.). siRNA duplexes were transfected using X-treme Gene transfection reagent from Roche or Lipofectamine 2000 from Invitrogen.

Immunohistochemistry

Immunohistochemistry was performed using Vectastain ABC Kit from Vector Laboratories (Burlingame, Calif.). Mouse Met antibody was used at a 1:100 dilution.

TABLE 3

Relative expression levels of HGF mRNA in the gastric cancer cell lines.

| Cell lines | Relative HGF expression |
|---|---|
| Amp+ cells | |
| MKN45 | nd |
| SNU-5 | nd |
| GTL16 | nd |
| KATO II | nd |
| Hs746T | 8.80 ± 2.29 |
| Amp− cells | |
| MKN74 | nd |
| SNU-16 | nd |
| HSC39 | 27.35 ± 5.35 |
| AGS | nd |
| KATO III | 1.67 ± 0.50 |
| SNU-1 | nd |
| N87 | 1.00 ± 0.27 |
| MKN1 | 2.22 ± 1.56 |
| MKN28 | nd |
| TMK-1 | 26.45 ± 2.31 |
| Hs738T | 4710.45 ± 121.48 |
| MKN7 | nd | nd - denotes "not detectable".

TABLE 4

Percent viability after 96 h treatment with 500 nM PHA-665752.

| Cell lines | % viability |
|---|---|
| Amp+ cells | |
| MKN45 | 5.8 ± 0.5 |
| SNU-5 | 4.0 ± 0.2 |
| GTL16 | 12.8 ± 1.2 |
| KATO II | 3.2 ± 0.3 |
| Hs746T | 38.4 ± 1.2 |
| Amp− cells | |
| MKN74 | 89.6 ± 2.6 |
| SNU-16 | 99.9 ± 1.5 |
| HSC39 | 92.8 ± 2.1 |
| AGS | 99.8 ± 1.9 |
| KATO III | 105.2 ± 9.5 |
| SNU-1 | 100.9 ± 3.2 |
| N87 | 86.0 ± 7.4 |
| MKN1 | 87.5 ± 4.0 |
| MKN28 | 103.8 ± 4.2 |
| TMK-1 | 91.3 ± 2.1 |
| Hs738T | 100.2 ± 12.3 |
| MKN7 | 117.9 ± 21.1 |

Example 2

Screening of Cancer Cell Lines for Sensitivity to a MET Tyrosine Kinase Inhibitor.

Figure 7:
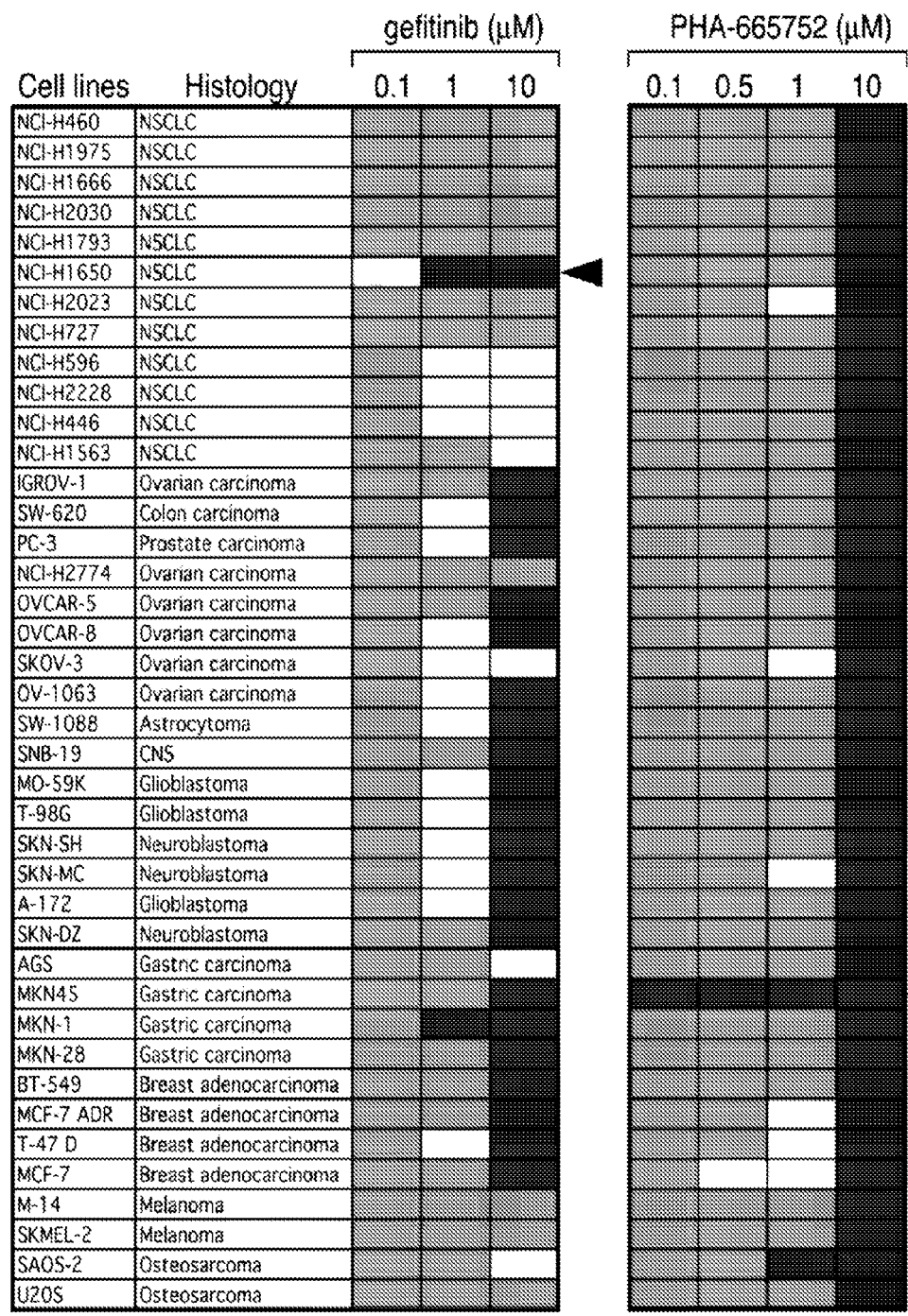
FIG. 7: Drug sensitivity profile of 40 human cancer cell lines treated with gefitinib or PHA-665752. Cells were cultured and analyzed in triplicate within microtiter plates. Cell numbers were quantitated by DNA staining, 3 days after addition of various concentrations of drugs and expressed as a fraction of matched untreated cultures. For each drug concentration, cell lines with relative drug sensitivity (<50% of untreated control growth) are shown in darkest staining, intermediate sensitivity (50-75%) in lightest shading, and drug insensitivity (>75%) in intermediate shading. Arrowheads denote cell lines with unique drug sensitivity to gefitinib (NCI-H1650) or to PHA-665752 (MKN45).

The genetic heterogeneity underlying differential responsiveness of lung cancers to the EGFR tyrosine kinase inhibitors gefitinib and erlotinib is recapitulated in lung-cancer-derived cell lines. Whereas most NSCLC cell lines have an IC50 for gefitinib of 10 μM, rare cell lines harboring activating mutations in EGFR typically demonstrate a 50- to 100-fold enhancement in sensitivity, as measured by cell killing (32, 38-40). To test the predictive value of such an in vitro drug-sensitivity screen, we treated 40 cell lines representing diverse tumor types with gefitinib at concentrations ranging from 100 nM to 10 μM. Extreme sensitivity (100 nM) was observed with NCI-H1650, the only NSCLC cell line in our panel with the del E746-A750 activating mutation in EGFR (FIG. 7) (39). Variable degrees of sensitivity were evident in other cell lines tested, but none had a degree of cell killing comparable to <1 μM gefitinib. The NCI-H1975 NSCLC cell line harbors both a L858R-sensitizing mutation in EGFR and the T790M drug-resistance mutation, and, hence, it scored as relatively resistant in the assay. Consistent with the lower gefitinib sensitivity of the remaining cell lines, they did not harbor activating EGFR mutations. To extend this analysis to other tyrosine kinase inhibitors, we screened the same cancer cell line panel for sensitivity to a specific MET tyrosine kinase inhibitor PHA-665752 (24) (Pfizer). Extreme sensitivity (100 nM) to this drug was observed for one gastric cancer cell line MKN45. As with gefitinib, other cell lines demonstrated variable degrees of cell killing, but none had a similar response <1 μM of PHA-665752 (FIG. 7). The MKN45 cell line is known to have amplification of MET (41), pointing to a potential genetic mechanism underlying its extraordinary drug sensitivity. None of the other 39 cell lines had MET gene amplification, as determined by quantitative PCR (qPCR) analysis (data not shown).

MET Amplification and Constitutive Activation in Human Gastric Cancer Cells.

Figure 8A:
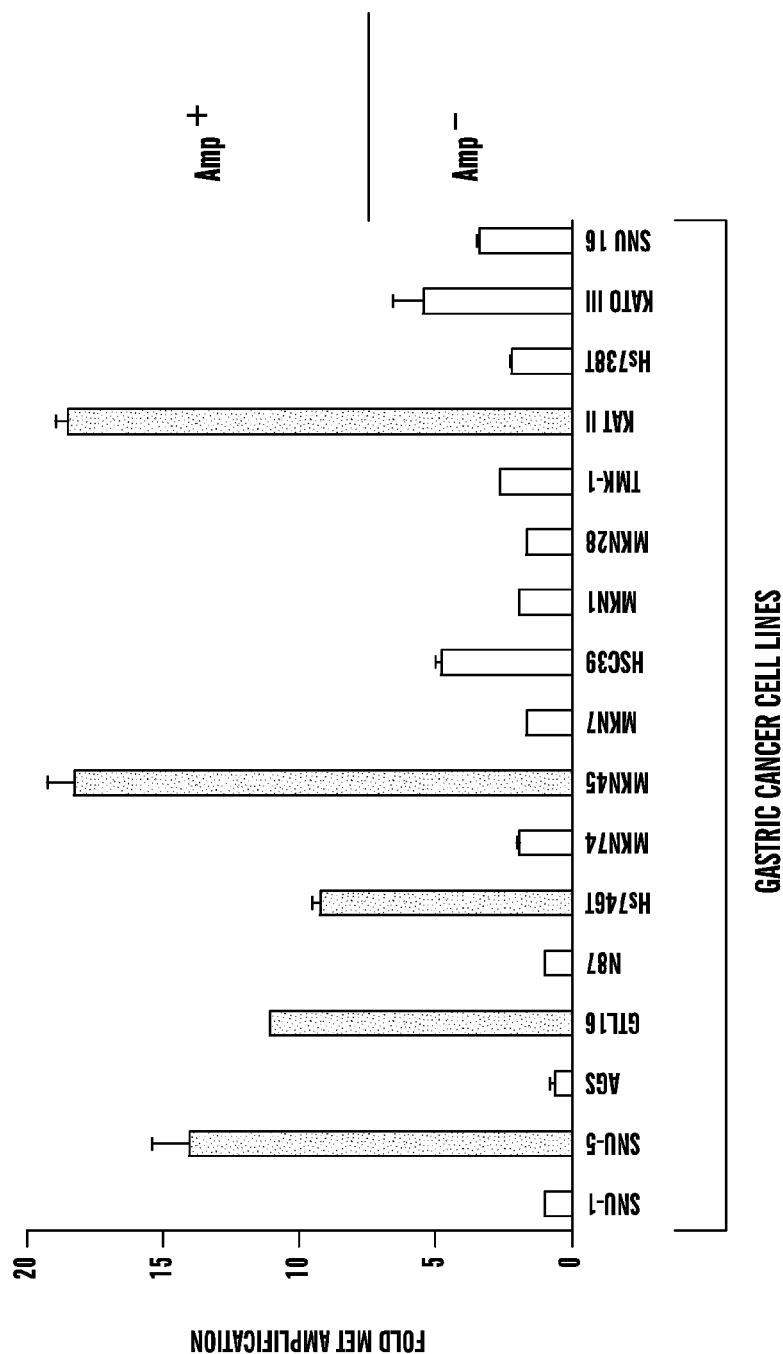
(FIG. 8A) Human gastric cancer cell lines screened for the presence of MET amplification by using qPCR. The relative MET copy number is derived by comparison with an unrelated control locus, TOP3A, at chromosome locus 17p11. Cell lines with high-level MET amplification (Amp+) are shown in darkest shading, whereas the cells with no or low-level copy number increase of MET (Amp−) are shown in lighter shading. All Amp+ cells have HSR-amplification of MET.
Figure 8B:
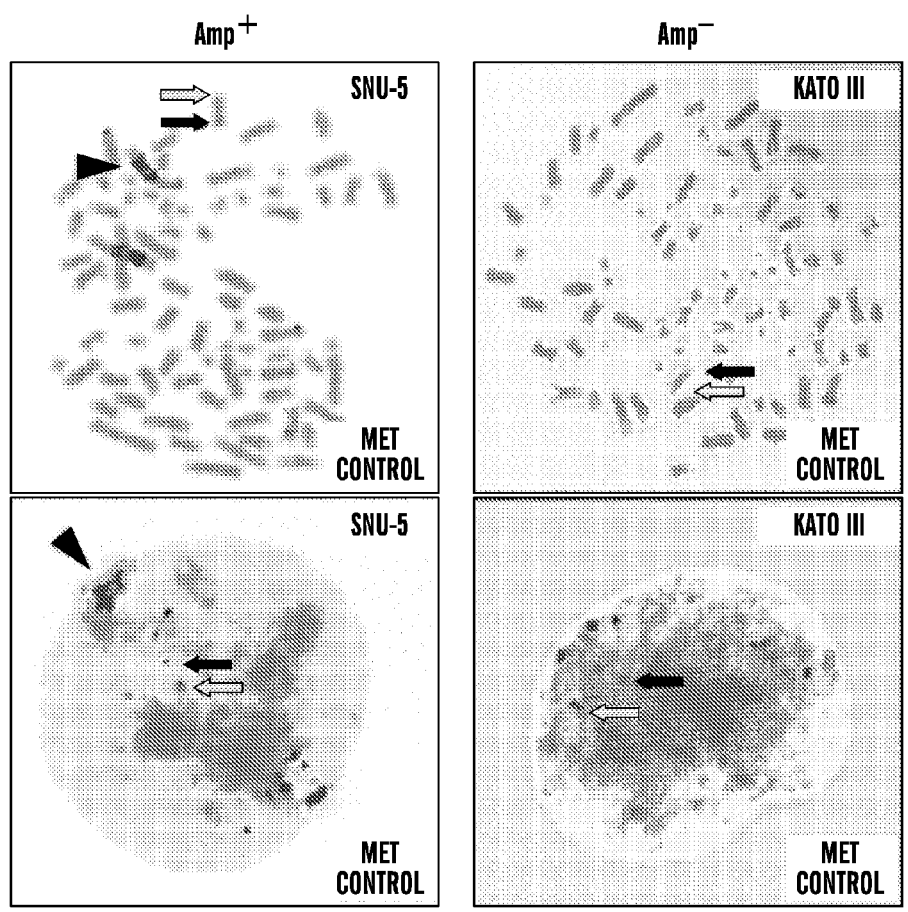
(FIG. 8B) Representative metaphase (Upper) and interphase (Lower) FISH analysis of human gastric cancer cell lines, showing amplification of MET within characteristic HSRs in Amp+ cells. In SNU-5 cells (Amp+) with high-level amplification, the MET signal is present in HSRs (darker arrowhead) that are distinct from the endogenous gene locus (chromosome 7q31, darker arrow). Control probe on the opposite arm of chromosome 7 (chromosome 7p21) is shown in green (lighter arrow). In KATO III cells (Amp−), the low-level increased MET gene copy number is associated with five individual copies of chromosome 7 (aneuploidy).

Overexpression of MET has been reported in many epithelial cancers, but gene amplification is most common in gastric cancer, where 10-20% of all primary tumors and up to 40% of the scirrhous histological subtype have increased MET gene copy numbers (21, 42-43). Analysis of a panel of gastric cancer cell lines by using qPCR identified increased MET gene copy number in 5 of 17 (29%) cases (FIG. 8A). In all 5 cell lines, FISH analysis showed the amplified gene copies to be integrated within a chromosomal locus, consistent with so-called homogeneously staining regions (HSRs) (FIG. 8B). HSR-amplification is characteristically stable in the absence of selection, indicating that the increased MET gene copy number represents targeted amplification of this locus rather than reflecting general aneuploidy. FISH and qPCR analyses were consistent in identifying the subset of cell lines with MET amplification, with higher fold amplification apparent by FISH (FIGS. 8 A and B), presumably reflecting the effect of low-level copy-number variability in the control locus used in qPCR analysis, resulting in underestimation of the true extent of MET amplification. A cutoff of 8-fold gene amplification, as measured by qPCR, provided a clear distinction between gastric cancer cells with low-level aneuploidy (Amp−) versus those with high-level specific HSR-amplification of MET (Amp+).

Figure 9A:
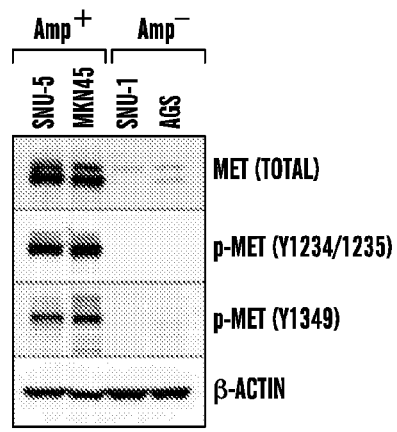
(FIG. 9A) MET is constitutively activated in the Amp+ cells. Immunoblotting analysis, demonstrating high levels of MET protein expression in two representative Amp+ cell lines, compared with two Amp− cell lines. Immunoblotting using two phospho-specific MET antibodies (against Y1234/1235 and Y1349) shows strong baseline phosphorylation of the receptor only in Amp+ cells (-actin loading control).
Figure 9B:
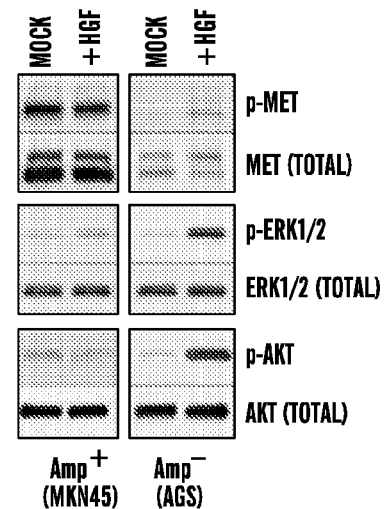
(FIG. 9B) Effect of HGF on MET activation in Amp+ and Amp− cells. Representative immunoblotting analysis of cells serum-starved for 24 h and treated with 40 ng/ml HGF for 10 min. Phosphorylation of MET (Y1234/1235) is induced by HGF in Amp− cells, but it is unaltered in Amp+ cells treated with HGF (total MET expression in these cells is shown as control). Phosphorylation of the downstream effectors ERK1/2 (T202/Y204) and AKT (S473) is also strongly induced in Amp− cells treated with HGF but unaltered by HGF treatment in Amp+ cells. Blots probed with phospho-specific antibodies were exposed for a short time to illustrate signaling differences and to avoid potential signal saturation associated with longer exposure times.
Figure 9C:
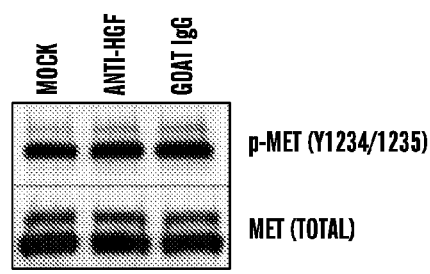
(FIG. 9C) Neutralizing HGF antibody does not affect MET activation in Amp+ cells. Representative Western blot, demonstrating unaltered baseline activation of MET in Amp+ cells (MKN45) treated with neutralizing anti-HGF antibody. Cells were serum starved for 24 h and subsequently treated with 5 μg/ml anti-HGF antibody or goat IgG control in serum-free media for another 24 h, by using standard conditions for neutralization of HGF (30).
Figure 9D:
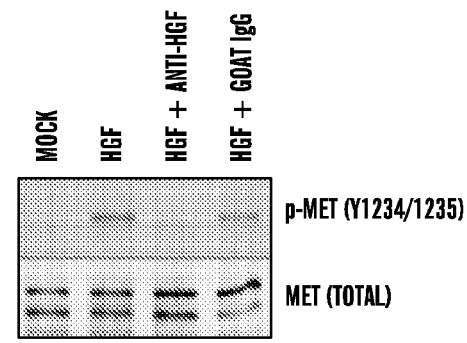
(FIG. 9D) Neutralizing HGF antibody can functionally inactivate HGF-mediated MET activation in Amp− cells. As control for C, Amp− cells (AGS) were treated with HGF alone, with neutralizing antibody to HGF, or goat IgG (control). Suppression of HGF-induced MET activation in Amp− cells confirms effective HGF neutralizing activity of this anti-HGF antibody.

As expected, all 5 Amp$^+$ cells displayed dramatic elevation in MET protein expression, compared with the 12 Amp− cells (FIG. 9A). Remarkably, Amp+ cells also displayed high levels of baseline MET activation, as measured by phosphorylation of tyrosine residues 1,234/1,235 and 1,349 (FIG. 9A). MET phosphorylation was not due to the presence of activating mutations, as determined by nucleotide sequencing of the entire coding sequence in all 17 gastric cancer cell lines (data not shown). MET activation in Amp+ cells also appeared to be independent of its ligand, hepatocyte growth factor (HGF)/scatter factor, based on three observations. First, whereas Amp− cells had low levels of MET phosphorylation under standard culture conditions but demonstrated HGF-induced receptor autophosphorylation accompanied by phosphorylation of downstream effectors ERK1/2 and AKT, no such increase in baseline MET phosphorylation or activation of downstream signaling was evident in Amp+ cells treated with HGF (FIG. 9B). Second, no HGF mRNA expression was detectable by quantitative RT-PCR in 4 of 5 Amp+ cell lines, arguing against an autocrine signaling loop. Finally, treatment of Amp+ cells with neutralizing anti-HGF antibody did not affect the levels of MET phosphorylation (FIG. 9C), whereas it effectively suppressed HGF-induced MET activation in Amp− cells (FIG. 9D). Thus, Amp+ cells appear to exhibit constitutive ligand-independent MET activation, which may result from receptor dimerization associated with the very high levels of protein expressed on the cell surface, an effect that has been reported for MET (22) and other receptor tyrosine kinases (23).

Figure 10A:
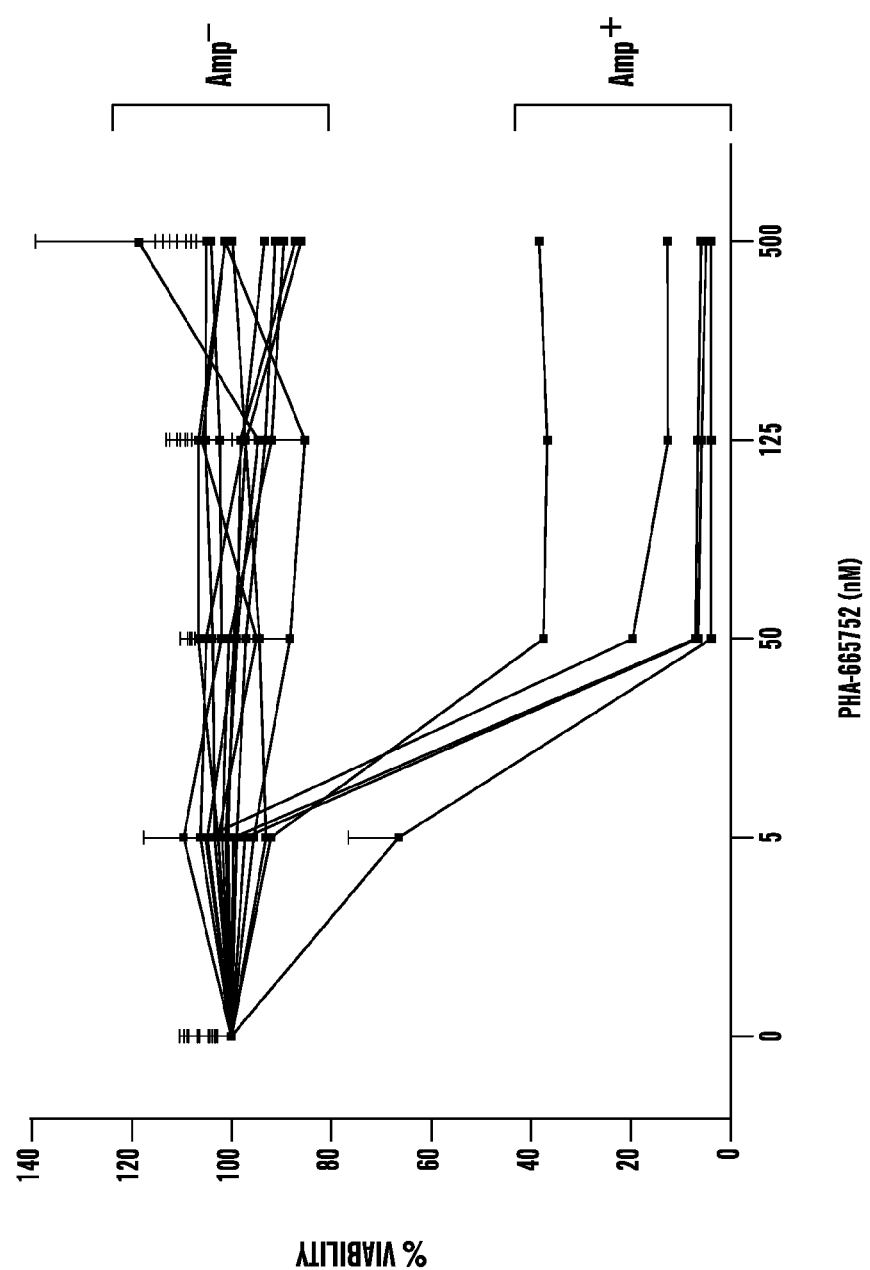
(FIG. 10A) Sensitivity of Amp+ cells and Amp-cells to increasing concentrations of PHA-665752. Cells were grown for 96 h at various concentrations of PHA-665752, and their viability was assessed by using MTT assays. Results are plotted as percent viability of treated cells compared with untreated matched controls. Experiments were performed in triplicate, with standard deviations shown.
Figure 10B:
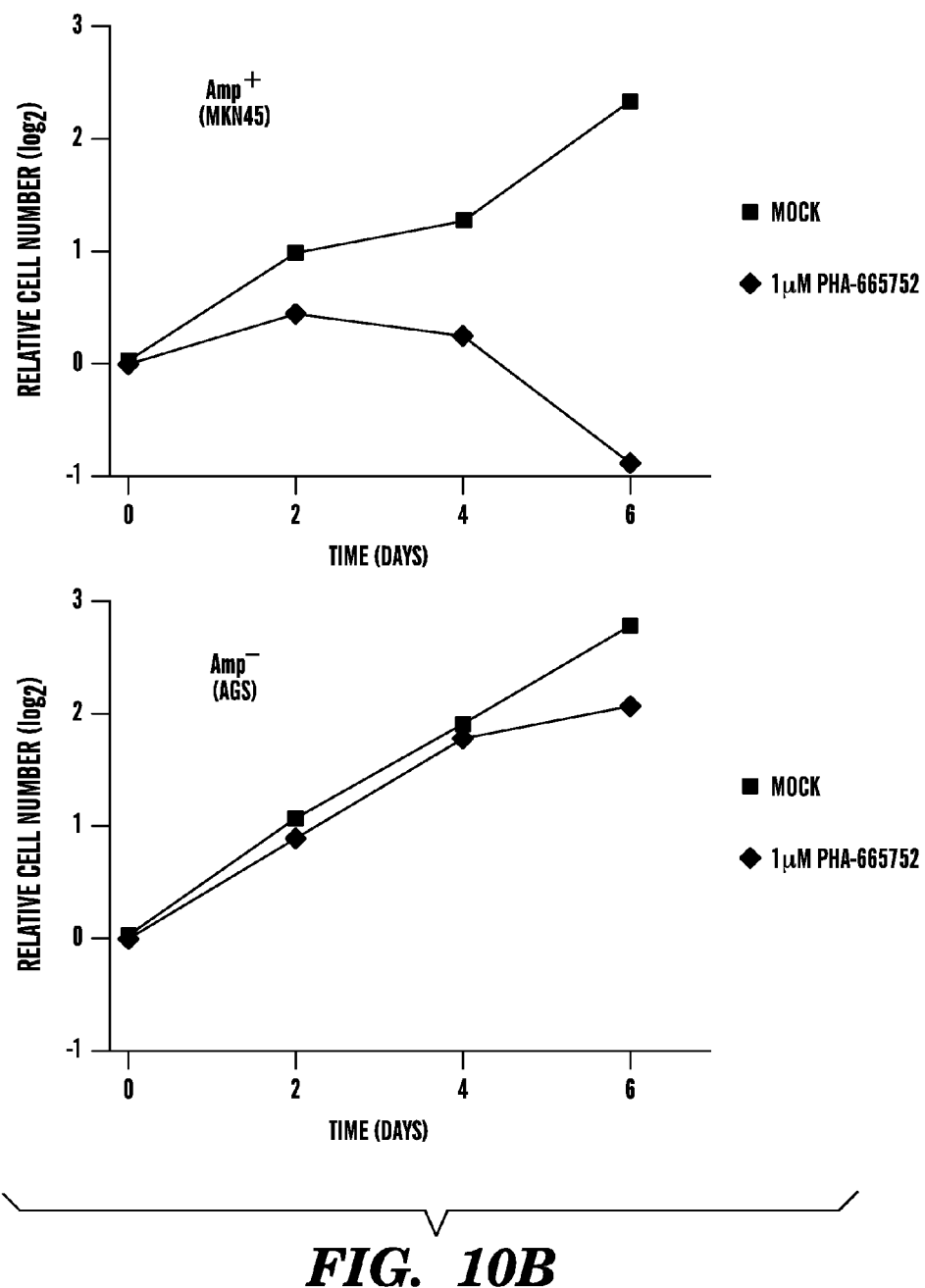
(FIG. 10B) Growth curve of representative Amp+ and Amp− cells treated with PHA-665752. Cells were grown for up to 6 days in the presence or absence of PHA-665752 (1 μM), and relative cell numbers were measured by using the fluorescent nucleic acid dye SYTO60 and expressed as a fraction of the number of cells plated. Experiments were performed in triplicate, with standard deviations shown.

MET Amplification As Molecular Marker of Susceptibility to a Tyrosine Kinase Inhibitor. To test the potential therapeutic relevance of these observations, we treated gastric cancer cell lines with the specific MET kinase inhibitor PHA-665752. This small-molecule inhibitor has an $IC_{50}$ against MET of 9 nM, compared with an $IC_{50}$ of 3.8 μM and >10 μM for EGFR and platelet-derived growth factor receptor, respectively (24). In 5 of 5 Amp+ cells, treatment with PHA-665752 for 96 h resulted in a dramatic reduction in cell numbers, whereas treatment had no effect in any of the 12 Amp− cells (P=0.00016, Fisher's exact test, two-sided) (FIG. 10A). Cell viability for these experiments was assessed by vital dye staining and expressed as a fraction of viable cells in matched untreated cultures. To determine whether this effect represented cell death or growth arrest, we compared the effect of PHA-665752 on the proliferation of Amp+ and Amp− cells as a function of time. Amp+ cells underwent an initial arrest in proliferation, followed by cell death (FIG. 10B). In contrast, the proliferation rate of Amp− cells was unaffected by the presence or absence of PHA-665752 (FIG. 10B).

Figure 10C:
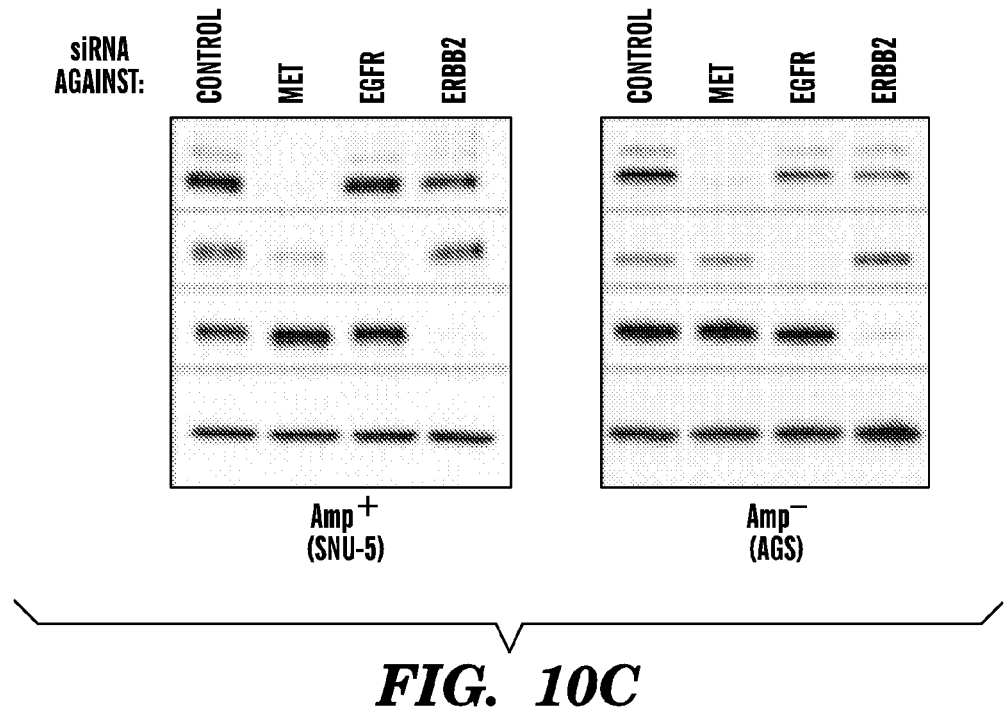
(FIG. 10C) Effective knockdown of targeted receptor tyrosine kinases by using siRNAs. Immunoblotting analysis of MET, EGFR, and ERBB2 protein levels after treatment of Amp+ and Amp− cells with specific siRNAs for 48 h. The relative exposure time of MET signal in Amp− immunoblots was increased to demonstrate effectiveness of siRNA knockdown (-actin loading control).
Figure 10D:
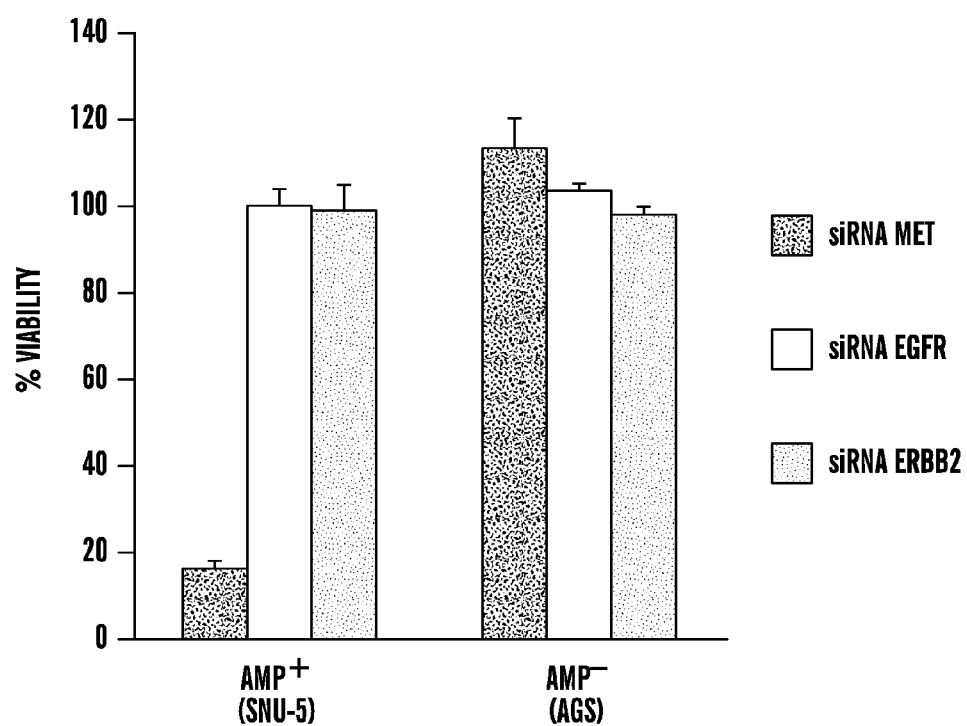
(FIG. 10D) Selective killing of Amp+ cells after siRNA-mediated knockdown of MET. Viability in Amp+ and Amp− cells, measured by using the MTT assay, was compared 96 h after knockdown of MET or unrelated receptors (EGFR and ERBB2). Cell viability is plotted as a percentage of cells treated with a nonspecific (control) siRNA duplex. Experiments were performed in triplicate, with standard deviations shown.

To confirm that the differential effects of PHA-665752 are truly attributable to its effect on MET, we transfected cells with small interfering (si)RNA targeting the MET receptor transcript. Effective and specific knockdown of MET protein expression was demonstrated by immunoblotting analysis (FIG. 10C). As control for nonspecific effects on growth factor signaling, we also tested siRNA targeting EGFR and ERBB2. Consistent with the effect of PHA-665752, a marked reduction in cell viability was evident in Amp+ cells after MET knockdown, whereas no such effect was observed in Amp− cells (FIG. 10D). Amp+ cells were not affected by knockdown of other receptors, such as EGFR or ERBB2.

Figure 11A:
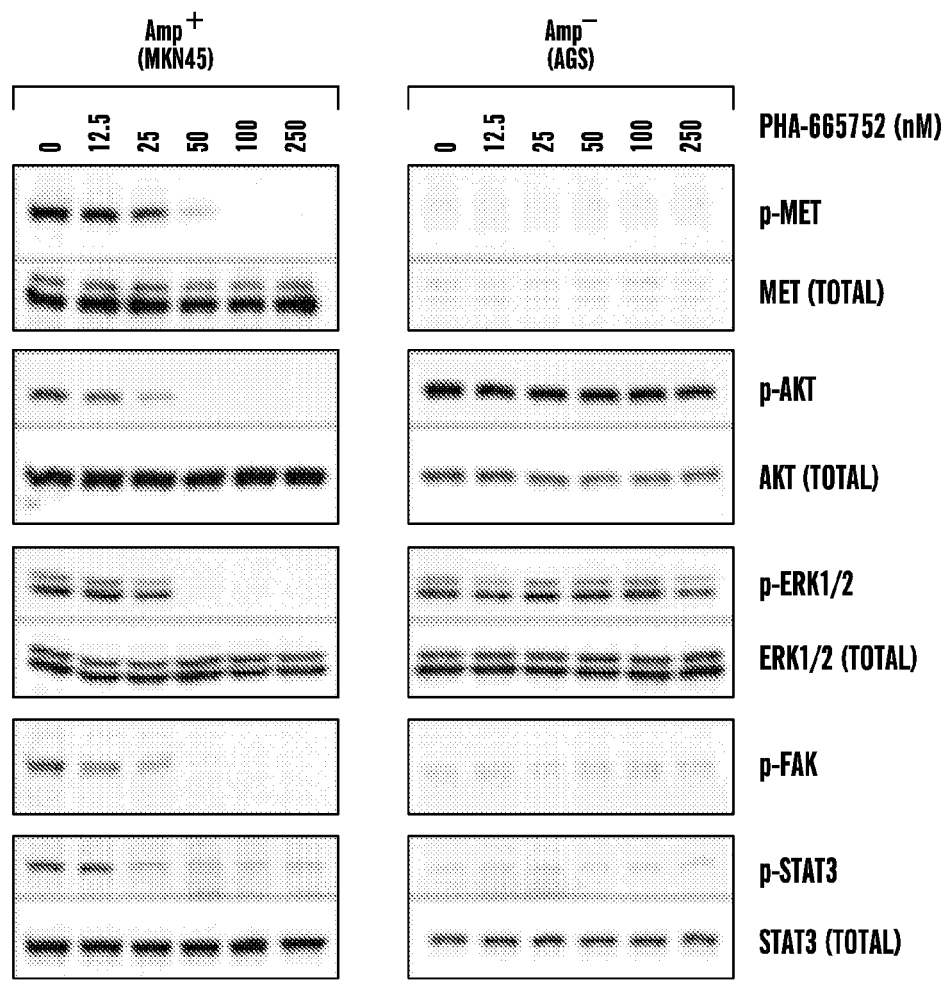
(FIG. 11A) Immunoblotting analysis, demonstrating inhibition of MET autophosphorylation (Y1234/1235) by PHA-665752. Abrogation of baseline phosphorylation of downstream effectors [ER1Z1/2 (T202/Y204), AKT (S473), STAT3 (Y727), and FAK (Y576/Y577)] is evident after drug treatment in Amp+ cells but not in Amp− cells. PHA-665752 was added for 3 h before protein extraction (representative blots shown).

To address the mechanism by which PHA-665752 triggers cell death in Amp+ cells, we first tested the effect of drug treatment on MET-dependent signaling. PHA-665752 (50 nM) effectively suppressed the constitutive MET autophosphorylation in Amp+ cells (FIG. 11A). Most significantly, treatment with this concentration of PHA-665752 also effectively abrogated the baseline phosphorylation of downstream effectors of growth factor receptors, such as ERK1/2, AKT, STAT3, and FAK. Thus, constitutive activation of these proliferative and survival pathways in Amp+ cells appears to depend specifically on baseline MET signaling. In contrast, in Amp− cells, where MET is not constitutively autophosphorylated, PHA-665752 had no effect on baseline phosphorylation of ERK1/2, AKT, STAT3, or FAK, indicating that these effectors are likely to be activated through alternative growth factor receptors (FIG. 11A).

Figure 11B:
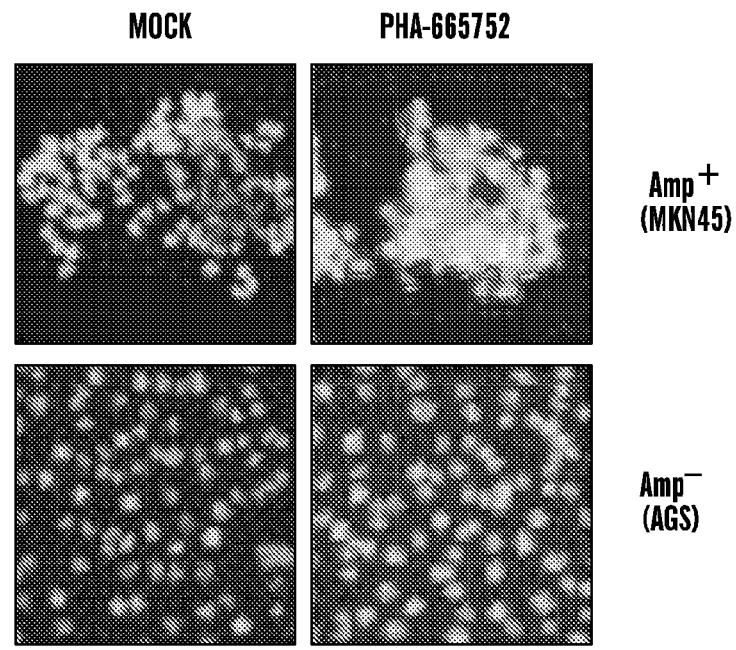
(FIG. 11B) Induction of apoptosis in Amp+ cells, but not in Amp− cells, 72 h after treatment with PHA-665752 (1 μM), measured by staining for cleaved caspase-3 (light staining). Cells are costained with DAPI to show nuclei.
Figure 11C:
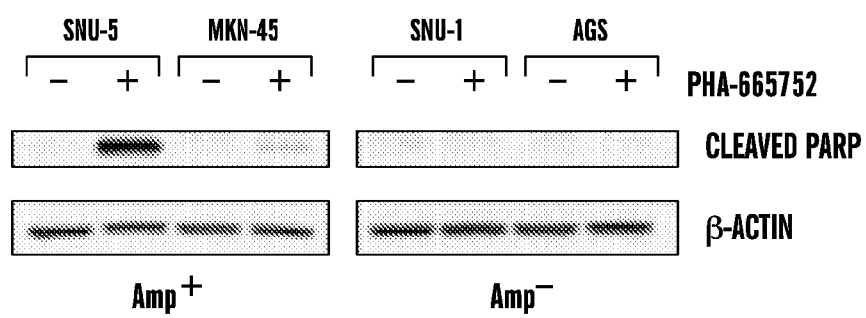
(FIG. 11C) Immunoblotting analysis for PARP cleavage to demonstrate induction of apoptosis in Amp+ cells, but not Amp− cells, after treatment with PHA-665752 (500 nM for 72 h) (-actin loading control).

Suppression of essential growth-factor-mediated survival pathways has been linked to the induction of apoptosis. Consistent with this model, both cleaved caspase-3-staining and PARP-cleavage assays demonstrated apoptosis in Amp+ cells treated with PHA-665752 but not in Amp− cells under identical conditions (FIGS. 11B and C). The early induction of apoptosis by PHA-665752 in SNU-5 cells is accompanied by a prominent PARP-cleavage signal at 72 h, compared with a more delayed but prolonged cell death in MKN45 cells (FIG. 9B). Thus, a subset of gastric cancer cell lines defined by targeted MET amplification appears to depend on constitutive activation of this growth factor receptor for their survival and show exquisite sensitivity to cell killing by the tyrosine kinase inhibitor PHA-665752.

Cellular Proliferation and Viability Assays. Cells were plated in 96-well plates in medium containing 4% FBS at 4,000 cells per well and, after 24 h, treated with various concentrations of either gefitinib or PHA-665752. For quantitation of cellular proliferation, cells were fixed at appropriate time points in 4% paraformaldehyde, and all plates were stained simultaneously by using the fluorescent nucleic acid stain SYTO60 (Molecular Probes) at 1:8,000 dilution in PBS. Quantitation was done by measuring the absorption at 700 nm by using the Odyssey Imaging System (LI-COR, Lincoln, Nebr.). The relative cell number was obtained by normalizing treated samples to matched untreated specimens. For quantitation of cell viability, cultures were stained after 4 days by using the MTT assay. Briefly, 10 μl of 5 mg/ml MTT (Thiazolyl blue) solution was added to each well and incubated for 2 h at 37° C. For adherent cell lines, the media was removed from each well, and the resultant MTT formazan was solubilized in 100 μl of DMSO. For nonadherent cell lines, the MTT formazan was solubilized by direct addition of 100 μl of acidic isopropanol (0.1 N HCl) to each well. The results were quantitated spectrophotometrically by using a test wavelength of 570 nm and a reference wavelength of 630 nm.

FISH and Mutational Analysis. Bacterial artificial chromosome clone CTD-1013N12, containing the full-length MET gene, was used for FISH. PAC RP4-620P6, mapping to 7p21, was used as a control probe. FISH was performed as described in ref. 44. For mutational analysis, genomic DNA was amplified by PCR and sequenced bidirectionally by using BigDye Terminator v1.1 chemistry (Applied Biosystems). Primer sequences and annealing temperatures are provided herein.

siRNA-Mediated "Knockdown" of MET Expression and Immunoblotting Analysis. The duplexes targeting MET, EGFR, and ERBB2 transcripts were custom SMARTpool mixtures from Dharmacon (Lafayette, Colo.). siRNA duplexes were transfected by using Lipofectamine 2000 from Invitrogen following the manufacturer's instructions. Briefly, cells were plated in 4% serum and transfected the next day with siRNAs at a final concentration of 40 nM for 5 h, followed by change of culture medium. The transfection was repeated on day 2 under the same conditions. Cell viability was assayed 4 days from the time of the first transfection, by using the MTT assay.

Antibodies. The phospho-MET (Y1234/Y1235), phospho-AKT (S473), phopho-ERK1/2(T202/Y204), phospho-FAK (Y576/Y577), phospho-STAT3 (Y727), AKT, ERK1/2, STAT3, ERBB2, EGFR, cleaved PARP, and cleaved caspase-3 antibodies were from Cell Signaling Technology (Beverly, Mass.). The phospho-MET (Y1349) antibody was from BioSource International (Camarillo, Calif.). The total MET antibody (C-12) was from Santa Cruz Biotechnology. The -actin antibody was from Abcam (Cambridge, Mass.). The neutralizing HGF goat antibody was from R & D Systems, and the matched goat IgG control antibody was from Sigma. All immunoblots were done with 1:1,000 antibody dilution, except for the -actin antibody, which was used at 1:10,000 dilution.

Apoptosis Induction Assay. Cells were plated on coverslips in 12-well dishes and grown to 75% confluency in 10% serum, followed by incubation in 4% serum and PHA-665752. After 72 h, cells were fixed with 4% paraformaldehyde for 20 min, permeabilized by using 1% Nonidet P-40 for 5 min, and blocked with 3% BSA for 30 min. The coverslips were then incubated overnight at 4° C. with cleaved caspase-3 antibody at 1:200 dilution. The next day, the coverslips were washed three times with PBS and incubated with a secondary antibody (goat anti-rabbit FITC-conjugated) for 1 h at 1:250 dilution. After five washes with PBS, coverslips were mounted in Vectashield mounting medium containing DAPI (Vector Laboratories), and staining was visualized by fluorescent microscopy.

REFERENCES

1. I. B. Weinstein, Science 297, 63 (2002).
2. S. G. Brodie et al., Oncogene 20, 7514 (2001).
3. X. Xu et al., Nat. Genet. 22, 37 (1999).
4. X. Xu, et al., Nat. Genet. 28, 266 (2001).
5. C. Brennan et al., Cancer Res. 64, 4744 (2004).
6. A. Bertotti, P. M. Comoglio, Trends Biochem. Sci. 28, 527 (2003).
7. C. Birchmeier, W. Birchmeier, E. Gherardi, G. F. Vande Woude, Nat. Rev. Mol. Cell. Biol. 4, 915 (2003).
8. P. C. Ma, G. Maulik, J. Christensen, R. Salgia, Cancer Metastasis Rev. 22, 309 (2003).
9. S. Rong et al., Mol. Cell. Biol. 12, 5152 (1992).
10. S. Rong, S. Segal, M. Anver, J. H. Resau, G. F. Vande Woude, Proc. Natl. Acad. Sci. U.S.A. 91, 4731 (1994).
11. R. Abounader et al., Faseb J. 16, 108 (2002).
12. L. Schmidt et al., Nat. Genet. 16, 68 (1997).
13. J. H. Lee et al., Oncogene 19, 4947 (2000).
14. I. Bieche, M. H. Champeme, R. Lidereau, Int. J. Cancer 82, 908 (1999).
15. E. Lengyel et al., Int. J. Cancer 113, 678 (2005).
16. J. Y. Kang et al., Cancer Res. 63, 1101 (2003).
17. M. I. Gallego, B. Bierie, L. Hennighausen, Oncogene 22, 8498 (2003).
18. M. Jeffers et al., Proc. Natl. Acad. Sci. U.S.A. 95, 14417 (1998).
19. H. Takayama et al., Proc. Natl. Acad. Sci. U.S.A. 94, 701 (1997).
20. M. Nakajima et al., Cancer 85, 1894 (1999).
21. H. Kuniyasu et al., Biochem. Biophys. Res. Commun. 189, 227 (1992).
22. J. D. Bergstrom, A. Hermansson, T. Diaz de Stahl, N. E. Heldin, Br. J. Cancer 80, 650 (1999).
23. P. J. Brennan, T. Kumagai, A. Berezov, R. Murali, M. I. Greene, Oncogene 19, 6093 (2000).
24. J. G. Christensen et al., Cancer Res. 63, 7345 (2003).
25. C. Ponzetto et al., Oncogene 6, 553 (1991).
26. A. Hellman et al., Cancer Cell 1, 89 (2002).
27. B. J. Druker et al., N. Engl. J. Med. 344, 1038 (2001).
28. B. J. Druker et al., N. Engl. J. Med. 344, 1031 (2001).
29. D. A. Tuveson et al., Oncogene 20, 5054 (2001).
30. S. Hirota et al., Science 279, 577 (1998).
31. T. J. Lynch et al., N. Engl. J. Med. 350, 2129 (2004).
32. J. G. Paez et al., Science 304, 1497 (2004).
33. C. Brennan et al., Cancer Res. 64, 4744 (2004).
34. S. G. Brodie et al., Oncogene 20, 7514 (2001).
35. A. S. Wong et al., Oncogene 20, 1318 (2001).
36. R. Warn et al., Exp. Cell Res. 267, 258 (2001).
37. N. Chattopadhyay, R. J. MacLeod, J. Tfelt-Hansen, E. M. Brown, Am. J. Physiol. Endocrinol. Metab. 284, E219 (2003).
38. Koizumi, F., Shimoyain a, T., Taguchi, F., Saijo, N. & Nishio, K. (2005) Int. J. Cancer 116, 36-44.
39. Sordella, R., Bell, D. W., Haber, D. A. & Settleman, J. (2004) Science 305, 1163-1167.
40. Tracy, S., Mukohara, T., Hansen, M., Meyerson, M., Johnson, B. E. & Janne, P. A. (2004) Cancer Res 64, 7241-7244.
41. Rege-Cambrin, G., Scaravaglio, P., Carozzi, F., Giordano, S., Ponzetto, C., Comoglio, P. M. & Saglio, G. (1992) Cancer Genet. Cytogenet 64, 170-173.
42. Nessling, M., Solinas-Toldo, S., Wilgenbus, K. K., Borchard, F. & Lichter, P. (1998) Genes Chromosomes Cancer 23, 307-316.
43. Sakakura, C., Mori, T., Sakabe, T., Ariyama, Y., Shinomiya, T., Date, K., Hagiwara, A., Yamaguchi, T., Takahashi, T. & Nakamura, Y., et al. (1999) Genes Chromosomes Cancer 24, 299-305.
44. Mohapatra, G., Moore, D. H., Kim, D. H., Grewal, L., Hyun, W. C., Waldman, F. M., Pinkel, D. & Feuerstein, B. G. (1997) Genes. Chromosomes Cancer 20, 311-319.

The references cited throughout the application are incorporated herein by reference in their entirety.

The invention claimed is:

1. A method for identifying a cancer in an individual that is susceptible to treatment with a Met tyrosine kinase inhibitor comprising:
   a. obtaining a fixed tissue sample comprising genomic DNA from an individual;
   b. contacting the tissue sample with a nucleic acid probe that comprises a nucleotide sequence consisting of TGGATAATTGTGTCTTTCTCTAG (SEQ ID NO: 3) and specifically hybridizes to Met gene DNA, and also comprises a fluorescent dye, to thereby form a hybridization complex comprising the nucleic acid probe and the Met gene DNA;
   c. detecting a fluorescent signal in the hybridization complex that is at least 8-fold higher than a fluorescent signal generated in a negative control sample which has an absence of Met gene amplification; and
   d. identifying the cancer as susceptible to treatment when the at least 8-fold higher fluorescent signal is detected in the hybridization complex.

2. A method for identifying a cancer in an individual that is susceptible to treatment with a Met tyrosine kinase inhibitor comprising:
   a. obtaining a fixed tissue sample comprising genomic DNA from an individual;
   b. contacting the tissue sample with a detectable nucleic acid probe that comprises a nucleotide sequence consisting of TGGATAATTGTGTCTTTCTCTAG (SEQ ID NO: 3) and specifically hybridizes to Met gene DNA to thereby form a hybridization complex comprising the nucleic acid probe and the Met gene DNA;
   c. measuring amplification of the Met gene in the tissue sample by detecting a signal from the probe in the hybridization complex and comparing to that of a control sample, with amplification being indicated by a minimum of about an 8-fold increase in Met gene copy number compared to a non-amplified copy number;
   d. identifying the cancer as susceptible to treatment when Met gene amplification is measured in the tissue sample, and identifying the cancer as resistant in the absence of Met gene amplification in the tissue sample; and
   e. administering a Met tyrosine kinase inhibitor to the individual if a minimum of about an 8-fold increase in Met gene copy number is measured in the tissue sample.

3. The method of any one of claim 1 or 2, further comprising quantitative amplification of a portion of the Met gene prior to step b) with primers comprising the nucleic acid sequence

```
                                          (SEQ ID NO: 1)
TGTTGCCAAGCTGTATTCTGTTTAC
and
                                          (SEQ ID NO: 2)
TCTCTGAATTAGAGCGATGTTGACA.
```

* * * * *

UNITED STATES PATENT AND TRADEMARK OFFICE
CERTIFICATE OF CORRECTION

PATENT NO.        : 8,652,786 B2                                                          Page 1 of 1
APPLICATION NO. : 11/887608
DATED             : February 18, 2014
INVENTOR(S)       : Haber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 898 days.

Signed and Sealed this

Twenty-ninth Day of September, 2015

Michelle K. Lee
*Director of the United States Patent and Trademark Office*